(12) United States Patent
Kuriyama et al.

(10) Patent No.: US 8,471,048 B2
(45) Date of Patent: Jun. 25, 2013

(54) RUTHENIUM CARBONYL COMPLEX HAVING TRIDENTATE LIGAND, ITS PRODUCTION METHOD AND USE

(75) Inventors: Wataru Kuriyama, Hiratsuka (JP); Takaji Matsumoto, Hiratsuka (JP); Yasunori Ino, Hiratsuka (JP); Osamu Ogata, Hiratsuka (JP)

(73) Assignee: Takasago International Corporation, Tokyo (JP)

( * ) Notice: Subject to any disclaimer, the term of this patent is extended or adjusted under 35 U.S.C. 154(b) by 287 days.

(21) Appl. No.: 13/121,990

(22) PCT Filed: Jun. 30, 2010

(86) PCT No.: PCT/JP2010/004301
§ 371 (c)(1),
(2), (4) Date: Mar. 31, 2011

(87) PCT Pub. No.: WO2011/048727
PCT Pub. Date: Apr. 28, 2011

(65) Prior Publication Data
US 2011/0237814 A1    Sep. 29, 2011

(30) Foreign Application Priority Data
Oct. 23, 2009    (JP) ................. 2009-244893

(51) Int. Cl.
*C07F 5/02*        (2006.01)
*C07F 15/00*    (2006.01)
*C07C 209/00*    (2006.01)
*C07C 29/00*    (2006.01)

(52) U.S. Cl.
USPC ............... 556/8; 568/648; 568/678; 568/814; 568/864; 564/393

(58) Field of Classification Search
USPC ... 568/648, 678, 814, 864; 564/393; 560/160; 556/8, 16
See application file for complete search history.

(56) References Cited

U.S. PATENT DOCUMENTS
2005/0107638 A1    5/2005    Abdur-Rashid

OTHER PUBLICATIONS

R. Celenligil-Cetin et al., "Decarbonylation of Acetone and Carbonate at a Pincer-Ligated Ru Center", Organometallics, vol. 24, pp. 186-189 (2005).
A.T. Radosevich et al., "Ligand Reactivity in Diarylamido/Bis(Phosphine) PNP Complexes of Mn(CO)3 and Re(C))3", Inorg. Chem, vol. 48, pp. 9214-9221 (2009).
A. Friedrich et al., "Iridium Olefin Complexes Bearing Dialkylamino/amido PNP Pincer Ligands: Synthesis, Reactivity, and Solution Dynamics", Organometallics, vol. 28, pp. 708-718 (2009).
L.A. van der Veen et al., "Origin of the Bite Angle Effect on Rhodium Diphosphine Catalyzed Hydroformylation", Organometallics, vol. 19, pp. 872-883 (2000).

*Primary Examiner* — Porfirio Nazario Gonzalez
(74) *Attorney, Agent, or Firm* — Edwards Wildman Palmer LLP; Peter F. Corless; Christine C. O'Day

(57) ABSTRACT

The present invention relates to a ruthenium carbonyl complex that is represented by the following Formula (1):

$$RuXY(CO)(L) \quad (1)$$

(in the Formula (1), X and Y, which may be the same or different from each other, represent an anionic ligand and L represents a tridentate aminodiphosphine ligand which has two phosphino groups and a —NH— group), its production method, and a method for production of alcohols by hydrogenation-reduction of ketones, esters, and lactones using the complex as a catalyst.
The ruthenium carbonyl complex of the invention has a high catalytic activity and it can be easily prepared and handled.

18 Claims, 1 Drawing Sheet

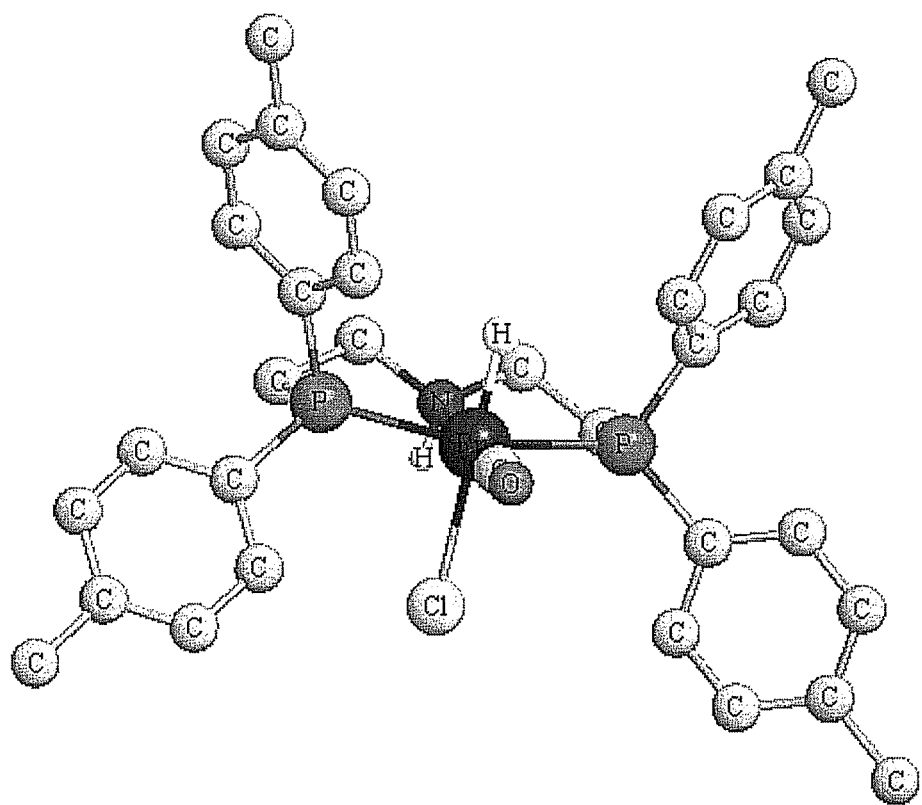

RUTHENIUM CARBONYL COMPLEX HAVING TRIDENTATE LIGAND, ITS PRODUCTION METHOD AND USE

CROSS-REFERENCES TO RELATED APPLICATIONS

This application is a 35 U.S.C. §371 U.S. national entry of International Application PCT/JP2010/004301 having an International filing date of Jun. 30, 2010, which claims priority of Japanese Patent Application No. 2009-244893 filed on Oct. 23, 2009, the contents of each of said applications being incorporated into this description by reference.

TECHNICAL FIELD

The present invention relates to a novel ruthenium carbonyl complex having a tridentate ligand which contains two phosphino groups and a —NH— group, its production method, and a method for production of alcohols by hydrogenation-reduction of ketones, esters, or lactones using the complex as a catalyst.

BACKGROUND ART

A method of obtaining alcohols by reducing ketones, esters, and lactones is important in chemical synthesis. In terms of reduced by-product formation, good operatability, and work safety, etc., reduction by catalytic hydrogenation is useful as a method for production of alcohols. Further, optically active alcohols are important as physiologically active materials such as pharmaceuticals, agrochemical agents, and aromachemicals, etc. and also as their synthetic intermediates. Asymmetric hydrogenation of ketones or hydrogenation-reduction of optically active esters is useful as a method for production of optically active alcohols. Ruthenium complexes having polydentate ligands are one of such reducing catalysts.

As for the ruthenium complex having a tridentate ligand which contains two phosphino groups and a —NH— group, a dichloro complex is described in Patent Document 1. Further, in Non-patent Document 1, a dichloro complex or a hydride complex having a trimethyl phosphine as a ligand is described. However, these complexes do not have a carbonyl ligand. Further, although a ruthenium complex having a tridentate ligand which contains two phosphino groups and a pyridine ring and a carbonyl ligand has been reported in Non-patent Documents 2, 3 and 4, no —NH— group is contained in the tridentate ligand.

With regard to the ruthenium dichloro complex disclosed in Patent Document 1, it is reported that ketones are hydrogenated and reduced in the presence of a base to give alcohols. However, no description is included regarding the reduction of esters or lactones. The ruthenium phosphine complex disclosed in Non-patent Document 1 is reported as a catalyst for dehydrogenation of ammonia-borane. However, hydrogenation-reduction of ketones, esters, and lactones is not described. Further, as the ruthenium phosphine complex has been reported to be unstable, its industrial application is difficult due to disadvantage in handling. Further, although it has been reported that the ruthenium complex having a pyridine ring as disclosed in Non-patent Document 2 or Non-patent Document 3 can catalyze the hydrogenation-reduction of esters or the ester synthesis reaction based on dehydrogenation of alcohols, there is a problem in that not only low temperature is required for the synthesis of the complex but also complicate procedures and the radical reaction using a tin compound, which is undesirable in terms of industrial application, are used for the synthesis of the ligand, etc. In particular, because the ruthenium complex having a pyridine ring described in Non-patent Document 2 has low catalytic activity for hydrogenation-reduction of esters, development of a catalyst having higher catalytic activity has been waited for.

PRIOR ART DOCUMENTS

Patent Documents

[Patent Document 1] US 2005/0107638 A1

Non-Patent Documents

[Non-patent Document 1] Angew. Chem. Int. Ed. 2009, 48, p. 905-907
[Non-patent Document 2] Angew. Chem. Int. Ed. 2006, 45, p. 1113-1115
[Non-patent Document 3] J. Am. Chem. Soc. 2005, 127, p. 10840-10841
[Non-patent Document 4] Organometallics. 2004, 23, p. 4026-4033

SUMMARY OF THE INVENTION

Problems to be Solved by the Invention

An object of the invention is to provide a novel ruthenium complex which can be prepared and handled easily and obtained with relatively low cost, its production method, and a technique of producing alcohols by hydrogenation-reduction of ketones, esters, and lactones using the complex as a catalyst.

Means for Solving the Problems

Under the circumstances, as a result of intensive studies, the inventors of the invention developed a novel ruthenium complex having a tridentate ligand which contains two phosphino groups and a —NH— group and a carbonyl ligand. The ligands and the complex can be easily synthesized, have high stability, and can be easily handled.

Further, the inventors found that the ruthenium complex developed according to the invention has high catalytic activity for the hydrogenation-reduction of ketones, esters, and lactones, and therefore completed the invention.

In more detail, the invention is related to the following [1] to [18].

[1] A ruthenium carbonyl complex that is represented by the following Formula (1):

(in the Formula (1), X and Y, which may be the same or different from each other, represent an anionic ligand and L represents a tridentate aminodiphosphine ligand represented by the following Formula (2):

(in the Formula (2), $R^1$, $R^2$, $R^3$, and $R^4$, which may be the same or different from each other, represent a hydrogen atom, an alkyl group, a cycloalkyl group, an aryl group, an aralkyl group, an alkyloxy group, a cycloalkyloxy group, an aryloxy group, an aralkyloxy group, a heterocyclic group, or a substituted amino group, and $R^1$ and $R^2$ or $R^3$ and $R^4$ may bind to each other to form a ring with an adjacent phosphorus atom. Further, the alkyl group, cycloalkyl group, aryl group, aralkyl group, alkyloxy group, cycloalkyloxy group, aryloxy group, aralkyloxy group, heterocyclic group, and substituted amino group may have a substituent group. $Q^1$ and $Q^2$, which may be the same or different from each other, represent a divalent alkylene group which may have a substituent group, a divalent cycloalkylene group which may have a substituent group, or a divalent aralkylene group which may have a substituent group)).

[2] The ruthenium carbonyl complex according to [1], wherein the tridentate aminodiphosphine ligand L is represented by the following Formula (3):

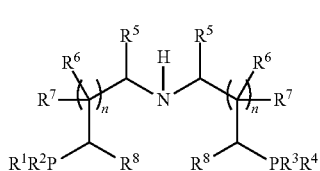

(in the Formula (3), $R^5$, $R^6$, $R^7$ and $R^8$, which may be the same or different from each other, represent a hydrogen atom, an alkyl group which may have a substituent group, a cycloalkyl group which may have a substituent group, an aryl group which may have a substituent group, or an aralkyl group which may have a substituent group. n represents an integer of 0 to 3).

[3] The ruthenium carbonyl complex according to [1], wherein the tridentate aminodiphosphine ligand L is represented by the following Formula (4):

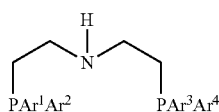

(in the Formula (4), $Ar^1$, $Ar^2$, $Ar^3$, and $Ar^4$, which may be the same or different from each other, represent an aryl group or an aromatic heterocyclic group. The aryl group and aromatic heterocyclic group may have a substituent group).

[4] The ruthenium carbonyl complex according to [3], wherein $Ar^1$, $Ar^2$, $Ar^3$, and $Ar^4$ in the Formula (4) is a phenyl group which may have a substituent group.

[5] The ruthenium carbonyl complex according to any one of [1] to [4], wherein the tridentate aminodiphosphine ligand L is represented by the following Formula (5):

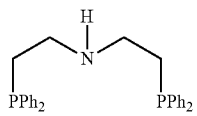

(in the Formula, Ph represents a phenyl group).

[6] The ruthenium carbonyl complex according to [1] or [2], wherein the tridentate aminodiphosphine ligand L is optically active.

[7] The ruthenium carbonyl complex according to any one of [1] to [6], wherein the anionic ligand X is a hydride and the anionic ligand Y is a chloride ion in the Formula (1).

[8] The ruthenium carbonyl complex according to any one of [1] to [6], wherein the anionic ligand X is a hydride and the anionic ligand Y is $BH_4^-$ in the Formula (1).

[9] A method of producing the ruthenium carbonyl complex represented by the Formula (1) by reacting the tridentate aminodiphosphine ligand L represented by the Formula (2) and $RuXY(CO)(P(Ar^5)_3)_3$ (in the formula, $Ar^5$ may be the same or different from each other and represents an aryl group which may have a substituent group).

[10] The method according to [9], wherein $Ar^5$ is a phenyl group.

[11] The method according to [9] or [10], wherein the tridentate aminodiphosphine ligand L represented by the Formula (2) is a tridentate aminodiphosphine ligand L represented by the Formula (5).

[12] The method according to any one of [9] to [11], wherein $RuXY(CO)(P(Ar^5)_3)_3$ is $RuHCl(CO)(PPh_3)_3$.

[13] A method of producing a ruthenium carbonyl complex represented by the following Formula (6) by reacting $RuHCl(CO)(PPh_3)_3$ and a tridentate aminodiphosphine ligand L represented by the Formula (5):

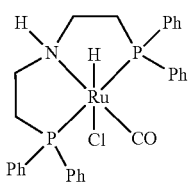

[14] A method of producing a ruthenium carbonyl complex represented by the following Formula (7) by reacting the ruthenium carbonyl complex represented by the Formula (6) and $NaBH_4$:

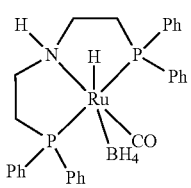

[15] A method of producing alcohols according to the hydrogenation-reduction of ketones by using a hydrogen donor in the presence of the ruthenium carbonyl complex according to any one of [1] to [8].

[16] A method of producing optically active alcohols according to the asymmetric hydrogenation-reduction of ketones by using a hydrogen donor in the presence of the ruthenium carbonyl complex according to any one of [6] to [8].

[17] A method of producing alcohols according to the hydrogenation-reduction of esters or lactones by using a hydrogen donor in the presence of the ruthenium carbonyl complex according to any one of [1] to [8].

[18] A method of producing optically active alcohols according to the hydrogenation-reduction of optically active esters or optically active lactones by using a hydrogen donor in the presence of the ruthenium carbonyl complex according to any one of [1] to [8] while maintaining the optical activity of the esters or the lactones.

Effects of the Invention

The novel ruthenium carbonyl complex of the invention can be easily prepared from a tridentate aminodiphosphine ligand and a precursor ruthenium carbonyl complex, and the tridentate aminodiphosphine ligand can be easily prepared by reacting a bisalkylamine having a leaving group with a phosphine compound in the presence of a base. Further, the precursor ruthenium carbonyl complex can be easily prepared from an inorganic ruthenium compound that is easily obtainable. Accordingly, the ruthenium carbonyl complex of the invention can be easily prepared and has high stability and good handleability, and therefore it is suitable for industrial application. The ruthenium carbonyl complex of the invention exhibits high catalytic activity even under a relatively mild reaction condition, and it can catalyze the hydrogenation-reduction of ketones, esters, or lactones in the presence of a hydrogen donor to produce alcohols with high yield. Further, if an optically active ligand is used, optically active alcohols can be synthesized according to asymmetric hydrogenation-reduction of ketones. Still further, even when the esters or lactones to be hydrogenated and reduced are optically active substances, they can be reduced to optically active alcohols without being accompanied with a significant decrease in the optical purity.

BRIEF DESCRIPTION OF THE DRAWINGS

FIG. 1 represents a schematic drawing of the chemical structure of the ruthenium carbonyl complex 18 of the invention based on the X ray structure analysis of the complex 18.

MODES FOR CARRYING OUT THE INVENTION

First, the ruthenium carbonyl complex of the invention that is represented by the following Formula (1) will be explained.

(in the Formula (1), X and Y, which may be the same or different from each other, represent an anionic ligand and L represents a tridentate aminodiphosphine ligand that is represented by the following Formula (2)).

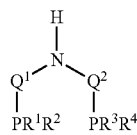

(in the Formula (2), $R^1$, $R^2$, $R^3$, and $R^4$, which may be the same or different from each other, represent a hydrogen atom, an alkyl group, a cycloalkyl group, an aryl group, an aralkyl group, an alkyloxy group, a cycloalkyloxy group, an aryloxy group, an aralkyloxy group, a heterocyclic group, or a substituted amino group, and $R^1$ and $R^2$ or $R^3$ and $R^4$ may bind to each other to form a ring with an adjacent phosphorus atom. Further, the alkyl group, cycloalkyl group, aryl group, aralkyl group, alkyloxy group, cycloalkyloxy group, aryloxy group, aralkyloxy group, and heterocyclic group may have a substituent group, respectively. $Q^1$ and $Q^2$, which may be the same or different from each other, represent a divalent alkylene group which may have a substituent group, a divalent cycloalkylene group which may have a substituent group, or a divalent aralkylene group which may have a substituent group).

Explanations will be given to the tridentate aminodiphosphine ligand that is used in the invention. Examples of the tridentate aminodiphosphine ligand, that is expressed as L in the Formula (1), include a ligand which contains two phosphino groups and a —NH— group. Specific examples of the tridentate aminodiphosphine ligand include the ligand that is represented by the above Formula (2).

Explanations will be given to $R^1$, $R^2$, $R^3$, and $R^4$ in the Formula (2).

Examples of the alkyl group include a linear or branched alkyl group which contains 1 to 50 carbon atoms, preferably 1 to 20 carbon atoms, and more preferably 1 to 10 carbon atoms, such as a methyl group, an ethyl group, a n-propyl group, an isopropyl group, a n-butyl group, an isobutyl group, a s-butyl group, a tert-butyl group, a n-pentyl group, a n-hexyl group, and a n-octyl group.

Further, examples of the cycloalkyl group include a monocyclic, polycyclic, or condensed-cyclic cycloalkyl group which contains 3 to 30 carbon atoms, preferably 3 to 20 carbon atoms, and more preferably 3 to 10 carbon atoms, such as a cyclopropyl group, a cyclopentyl group, and a cyclohexyl group.

Further, examples of the aryl group include a monocyclic, polycyclic, or condensed-cyclic aryl group which contains 6 to 36 carbon atoms, preferably 6 to 18 carbon atoms, and more preferably 6 to 14 carbon atoms. Specifically, the examples include a phenyl group, a naphthyl group, an anthryl group, a phenanthryl group, and a biphenyl group.

Further, examples of the aralkyl group include the alkyl group described above in which at least one hydrogen atom is substituted with the aryl group described above, and preferred examples include an aralkyl group which contains 7 to 15 carbon atoms. Specific examples include a benzyl group, a 1-phenylethyl group, a 2-phenylethyl group, a 1-phenylpropyl group, and a 3-naphthylpropyl group.

Further, examples of the alkyloxy group include an alkyloxy group made of a linear or branched alkyl group which contains 1 to 20 carbon atoms, preferably 1 to 15 carbon atoms, and more preferably 1 to 10 carbon atoms, such as a methoxy group, an ethoxy group, a n-propoxy group, an isopropoxy group, a n-butoxy group, an isobutoxy group, a s-butoxy group, a tert-butoxy group, and a n-pentyloxy group.

Further, examples of the cycloalkyloxy group include a cycloalkyloxy group made of a polycyclic or condensed-cyclic cycloalkyl group which contains 3 to 20 carbon atoms, preferably 3 to 15 carbon atoms, and more preferably 3 to 10 carbon atoms, such as a cyclopropyloxy group, a cyclopentyloxy group, and a cyclohexyloxy group.

Further, examples of the aryloxy group include an aryloxy group made of a monocyclic, polycyclic, or condensed-cyclic aryl group which contains 6 to 36 carbon atoms, preferably 6 to 18 carbon atoms, and more preferably 6 to 14 carbon atoms, and specific examples include a phenoxy group, a tolyloxy group, a xylyloxy group, and a naphthoxy group.

Further, examples of the aralkyloxy group include the alkyloxy group described above in which at least one hydrogen atom of the alkyl group or cycloalkyl group is substituted with the aryl group described above, and it is preferably an aralkyloxy group having 7 to 15 carbon atoms. Specific examples include a benzyloxy group, a 1-phenylethoxy group, a 2-phenylethoxy group, a 1-phenylpropoxy group, a 2-phenylpropoxy group, a 3-phenylpropoxy group, a 4-phenylbutoxy group, a 1-naphthylmethoxy group, and a 2-naphthylmethoxy group.

Further, examples of the heterocyclic group include an aliphatic heterocyclic group and an aromatic heterocyclic group. Examples of the aliphatic heterocyclic group include a 3 to 8-membered, and preferably 4 to 6-membered monocyclic aliphatic heterocyclic group, polycyclic or condensed-cyclic aliphatic heterocyclic group having 2 to 14 carbon atoms in which at least one, or preferably 1 to 3 heteroatoms such as a nitrogen atom, an oxygen atom and/or a sulfur atom are included as a heteroatom. Specific examples of the aliphatic heterocyclic group include an azetidyl group, an azetidino group, a pyrrolidyl group, a pyrrolidino group, a piperidinyl group, a piperidino group, a piperazinyl group, a piperazino group, a morpholinyl group, a morpholino group, a tetrahydrofuryl group, a teterahydropyranyl group, and a tetrahydrothiophenyl group.

Further, examples of the aromatic heterocyclic group include a 5 or 6-membered monocyclic heteroaryl group, polycyclic or condensed-cyclic heteroaryl group having 2 to 15 carbon atoms in which at least one, or preferably 1 to 3 heteroatoms such as a nitrogen atom, an oxygen atom and/or a sulfur atom are included as a heteroatom. Specific examples include a furyl group, a thienyl group, a pyridyl group, a pyrimidyl group, a pyrazyl group, a pyridazyl group, a pyrazolyl group, an imidazolyl group, an oxazolyl group, a thiazolyl group, a benzofuryl group, a benzothienyl group, a quinolyl group, an isoquinolyl group, a quinoxalyl group, a phthalazyl group, a quinazolyl group, a naphthiridyl group, a cinnolyl group, a benzimidazolyl group, a benzoxazolyl group, a benzothiazolyl group, an acridly group, and an acridinyl group.

Examples of the substituted amino group include an amino group in which the two hydrogen atoms of the amino group are substituted with the alkyl group, cycloalkyl group, aryl group, aralkyl group and/or heterocyclic group described above that are the same or different from each other. Specific examples include a dialkylamino group such as a N,N-diethylamino group and a N,N-diisopropylamino group; a dicycloalkylamino group such as a N,N-dicyclohexylamino group; a diarylamino group such as a N,N-diphenylamino group and a N-naphthyl-N-phenylamino group, and; a diaralkylamino group such as a N,N-dibenzylamino group. Further, the alkyl group, cycloalkyl group, aryl group, aralkyl group and heterocyclic group in the substituted amino group may have an additional substituent group.

Examples of the substituent group which may be included in the alkyl group, cycloalkyl group, aryl group, aralkyl group, alkyloxy group, cycloalkyloxy group, aryloxy group, aralkyloxy group, heterocyclic group, as well as the alkyl group, cycloalkyl group, aryl group, aralkyl group, and heterocyclic group on the substituted amino group include the alkyl group, cycloalkyl group, aryl group, aralkyl group, alkyloxy group, cycloalkyloxy group, aryloxy group, aralkyloxy group, heterocyclic group, and substituted amino group that are described above, a halogen atom, a silyl group, and a hydroxy group which is optionally protected.

Examples of the halogen atom as a substituent group for $R^1$, $R^2$, $R^3$, and $R^4$ include a fluorine atom, a chlorine atom, a bromine atom, and an iodine atom.

Examples of the silyl group as a substituent group for $R^1$, $R^2$, $R^3$, and $R^4$ include a group in which three hydrogen atoms of the silyl group are substituted with the alkyl group, cycloalkyl group, aryl group, or aralkyl group described above. Specific examples include a trimethylsilyl group, a triethylsilyl group, a t-butyldimethylsilyl group, a t-butyldiphenylsilyl group, and a triphenylsilyl group.

Examples of the hydroxy group which is optionally protected as a substituent group for $R^1$, $R^2$, $R^3$, and $R^4$ include a non-protected hydroxy group, or a silyl group such as a trimethylsilyl group, a tert-butyldimethylsilyl group, and a tert-butyldiphenylsilyl group, or a hydroxy group which may be protected with a typical hydroxy-protecting group that is generally used for peptide synthetics, etc. as described in Reference 1 (Protective Groups in Organic Synthesis Second Edition, JOHN WILEY & SONS, INC. 1991), such as a benzyl group and a methoxymethyl group.

$Q^1$ and $Q^2$ in the Formula (2) will be explained below.

Examples of the divalent alkylene group include a linear or branched divalent alkyl chain which contains 1 to 20 carbon atoms, preferably 1 to 10 carbon atoms, and more preferably 1 to 6 carbon atoms. Specific examples include a methylene group, an ethylene group, a trimethylene group, a tetramethylene group, and a pentamethylene group.

Further, examples of the divalent cycloalkylene group include a divalent group made of a monocyclic, polycyclic, or condensed-cyclic cycloalkyl group which contains 3 to 15 carbon atoms, preferably 3 to 10 carbon atoms, and more preferably 3 to 6 carbon atoms such as a cyclopropylene group, a cyclobutylene group, a cyclopentylene group, and a cyclohexylene group.

Further, examples of the divalent aralkylene group include a divalent group containing 7 to 11 carbon atoms in which one hydrogen atom is removed from the aryl group of the aralkyl group such as a benzyl group and a phenethyl group. Examples include a benzylene group (-Ph-CH$_2$—), a 2-phenylethylene group (-Ph-CH$_2$CH$_2$—), a 1-naphthylmethylene group (—Np—CH$_2$—), and a 2-naphthylmethylene group (—Np—CH$_2$—)(in the formulae, -Ph- represents a phenylene group and —Np— represents a naphthylene group).

Examples of the substituent group which may be included in the divalent alkylene group, divalent cycloalkylene group, or divalent aralkylene group include an alkyl group, a cycloalkyl group, an aryl group, an aralkyl group, an alkyloxy group, a cycloalkyloxy group, an aryloxy group, an aralkyloxy group, a heterocyclic group, and a halogen atom, a silyl group, a substituted amino group, and a hydroxy group which is optionally protected, which are the same as those described with regard to $R^1$, $R^2$, $R^3$ and $R^4$ of the above Formula (2),.

Next, the monovalent anionic ligand that is represented by X or Y in the Formula (1) will be explained.

Examples of the monovalent anionic ligand include a hydride, an alkyloxy group, a cycloalkyloxy group, an aryloxy group, an aralkyloxy group, a hydroxy group, an acyloxy group, a sulfonyloxy group, a halogen ion, $AlH_4^-$, $AlH_2(OCH_2CH_2OCH_3)_2^-$, $BH_4^-$, $BH_3CN^-$, $BH(Et)_3^-$, and $BH(sec-Bu)_3^-$. Preferred examples include $BH_4^-$, a hydride, or a chloride ion. Further, in the present specification, the hydride may be simply described as a hydrogen, and the halogen ion may be simply described as a halogen.

Examples of the acyloxy group include those expressed as ($R^aCO_2$). Examples of $R^a$ in the acyloxy group $R^aCO_2$ include a hydrogen atom, an alkyl group, a cycloalkyl group, an aryl group, and an aralkyl group. Examples of the alkyl group, cycloalkyl group, aryl group, and aralkyl group include an alkyl group, a cycloalkyl group, an aryl group, and an aralkyl group which are the same as those described with regard to $R^1$, $R^2$, $R^3$ and $R^4$ of the above Formula (2). These alkyl group, cycloalkyl group, aryl group, and aralkyl group may be substituted with an alkyl group, a cycloalkyl group, an aryl group, an aralkyl group, an alkyloxy group, a cycloalkyloxy group, an aralkyloxy group, an aryloxy group, and a heterocyclic group, and a halogen atom, a silyl group, a hydroxy group which is optionally protected, an amino group which is optionally protected, and the like, which are the same as those described with regard to $R^1$, $R^2$, $R^3$ and $R^4$ of the above Formula (2).

Examples of the amino group which is optionally protected as a substituent group for $R^a$ include a non-protected amino group; a mono- or dialkylamino group such as a N-methylamino group, a N,N-dimethylamino group, a N,N-diethylamino group, a N,N-diisopropylamino group, and a N-cyclohexylamino group; a mono- or diarylamino group such as a N-phenylamino group, a N,N-diphenylamino group, a N-naphthylamino group, and a N-naphthyl-N-phenylamino group; a mono- or diaralkylamino group such as a N-benzylamino group and a N,N-dibenzylamino group; an acylamino group such as a formylamino group, an acetylamino group, a propionyl amino group, a pivaloylamino group, a pentanoylamino group, a hexanoylamino group, and a benzoyl amino group; an alkoxycarbonylamino group such as a methoxycarbonylamino group, an ethoxycarbonylamino group, a n-propoxycarbonylamino group, a n-butoxycarbonylamino group, a tert-butoxycarbonylamino group, a pentyloxycarbonylamino group, and a hexyloxycarbonylamino group; an aryloxycarbonylamino group such as a phenyloxycarbonylamino group; and an aralkyloxycarbonylamino group such as a benzyloxycarbonylamino group. Examples of the amino group which may be further protected include an amino group that is protected with a typical amino-protecting group generally used for peptide synthesis, etc. as described in the above Reference 1.

Examples of $R^a$ include a methyl group, an ethyl group, a propyl group, a tert-butyl group, a trifluoromethyl group, a phenyl group, and a pentafluorophenyl group.

Examples of the sulfonyloxy group include those that are expressed as ($R^S SO_3$). Examples of $R^S$ in the sulfonyloxy group $R^S SO_3$ include those which are the same as $R^a$ of the acyloxy group.

Examples of the halogen ion include a fluoride ion, a chloride ion, a bromide ion, and an iodide ion. Preferably, it is a chloride ion and a bromide ion, and more preferably it is a chloride ion.

Examples of the preferred tridentate aminophosphine ligand include those that are represented by the following Formula (3).

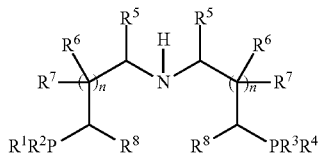

(in the Formula (3), $R^5$, $R^6$, $R^7$ and $R^8$, which may be the same or different from each other, represent a hydrogen atom, an alkyl group, a cycloalkyl group, an aryl group, or an aralkyl group, and $R^5$ and $R^5$, $R^5$ and $R^6$ or $R^7$ or $R^8$, $R^6$ and $R^7$ or $R^8$ may bind to each other to form a ring with an adjacent carbon atom. n represents an integer of 0 to 3. Further, the alkyl group, cycloalkyl group, aryl group, and aralkyl group may have a substituent group).

Examples of the alkyl group, cycloalkyl group, aryl group, and aralkyl group that are expressed as $R^5$, $R^6$, $R^7$ and $R^8$ in the Formula (3) include an alkyl group, a cycloalkyl group, an aryl group, and an aralkyl group which are the same as those described with regard to $R^1$, $R^2$, $R^3$ and $R^4$ of the above Formula (2). Further, examples of the substituent group that may be contained in these alkyl group, cycloalkyl group, aryl group, and aralkyl group include an alkyl group, a cycloalkyl group, an aryl group, an aralkyl group, an alkyloxy group, a cycloalkyloxy group, an aryloxy group, an aralkyloxy group, and a heterocyclic group, and a halogen atom, a silyl group, a substituted amino group, and a hydroxy group which is optionally protected, which are the same as those described with regard to $R^1$, $R^2$, $R^3$ and $R^4$ of the above Formula (2).

Examples of the more preferred tridentate aminodiphosphine ligand include those that are represented by the following Formula (4).

In the Formula (4), $Ar^1$, $Ar^2$, $Ar^3$, and $Ar^4$, which may be the same or different from each other, represent an aryl group or an aromatic heterocyclic group. Further, the aryl group and the aromatic heterocyclic group may have a substituent group.

Examples of the aryl group and aromatic heterocyclic group in the Formula (4) include an aryl group that is the same as the one described with regard to $R^1$, $R^2$, $R^3$ and $R^4$ of the above Formula (2) or an aromatic heterocyclic group that is the same as the one described for the heterocyclic group. Further, examples of the substituent group that may be contained in these aryl group or aromatic heterocyclic group include an alkyl group, a cycloalkyl group, an aryl group, an aralkyl group, an alkyloxy group, a cycloalkyloxy group, an aryloxy group, and an aralkyloxy group, and a halogen atom, a silyl group, a heterocyclic group, a substituted amino group, and a hydroxy group which is optionally protected, which are the same as those described with regard to $R^1$, $R^2$, $R^3$ and $R^4$ of the above Formula (2).

Further, examples of the still more preferred tridentate aminodiphosphine ligand include those that are represented by the following Formula (5).

Further, the tridentate aminodiphosphine ligand that is represented by the Formula (2) or (3) may be used as a ligand for the ruthenium carbonyl complex represented by the Formula (1) as an optically active substance depending on the substituent group on $Q^1$ or $Q^2$, or $R^1$ to $R^8$.

Examples of the ruthenium compound that is a starting material for producing the ruthenium carbonyl complex of the invention include, although not specifically limited, an inorganic ruthenium compound such as $RuCl_3$ hydrate, $RuBr_3$ hydrate, and $RuI_3$ hydrate, $RuCl_2(DMSO)_4$, [Ru(cod)Cl$_2$]n, [Ru(nbd)Cl$_2$]n, (cod)Ru(2-methallyl)$_2$, [Ru(benzene)Cl$_2$]$_2$, [Ru(benzene)Br$_2$]$_2$, [Ru(benzene)I$_2$]$_2$, [Ru(p-cymene)Cl$_2$]$_2$, [Ru(p-cymene)Br$_2$]$_2$, [Ru(p-cymene)I$_2$]$_2$, [Ru(mesitylene)Cl$_2$]$_2$, [Ru(mesitylene)Br$_2$]$_2$, [Ru(mesitylene)I$_2$]$_2$, [Ru(hexamethylbenzene)Cl$_2$]$_2$, [Ru(hexamethylbenzene)Br$_2$]$_2$, [Ru(hexamethylbenzene)I$_2$]$_2$, $RuCl_2(PPh_3)_3$, $RuBr_2(PPh_3)_3$, RuI$_2$(PPh$_3$)$_3$, RuH$_4$(PPh$_3$)$_3$, RuClH(PPh$_3$)$_3$, RuH(OAc) (PPh$_3$)$_3$, and RuH$_2$(PPh$_3$)$_4$. In the exemplified compounds, DMSO, cod, nbd, and Ph represents dimethyl sulfoxide, 1,5-cyclooctadiene, norbornadiene, and a phenyl group, respectively.

The ruthenium carbonyl complex represented by the Formula (1) can be easily prepared from the tridentate aminodiphosphine ligand and the precursor ruthenium carbonyl complex.

The tridentate aminodiphosphine ligand can be easily prepared by reacting bis(substituted alkyl) amine having a leaving group with an alkali metal phosphido compound of lithium, sodium, and potassium, etc.

The precursor ruthenium carbonyl complex can be obtained in accordance with the method described in Inorg. Synth, 1974, 15, 45, for example. By reacting the obtained precursor ruthenium carbonyl complex with the tridentate aminodiphosphine ligand, the ruthenium carbonyl complex of the invention having the tridentate aminodiphosphine ligand can be provided.

Examples of the precursor ruthenium carbonyl complex include carbonyl(dihydride) tris(triphenylphosphine) ruthenium (II), carbonylchlorohydride tris(triphenylphosphine)ruthenium(II), and carbonyldichlorohydride tris(triphenylphosphine) ruthenium (II).

For example, the ruthenium carbonyl complex represented by the Formula (1) can be produced by reacting the tridentate aminodiphosphine ligand L represented by the Formula (2) with RuXY(CO)(P(Ar$^5$)$_3$)$_3$ (in the formula, Ar$^5$ may be the same or different from each other and represents an aryl group which may have a substituent group). Examples of the aryl group or the substituent group in Ar$^5$ include those described above. Preferred examples of Ar$^5$ include a phenyl group which may have a substituent group, in particular a phenyl group.

Further, the ruthenium carbonyl complex in which X in the ruthenium carbonyl complex represented by the Formula (1) is BH$_4^-$ can be produced by reacting the ruthenium carbonyl complex having a chloride ion as X with NaBH$_4$.

The complex produced by the above described method may result in a stereoisomer depending on the coordination type or the conformation of a ligand. However, the complex used for the reaction can be a mixture of the stereoisomers or a pure isomer.

Further, the ruthenium carbonylhydride borohydride complex having the tridentate aminodiphosphine ligand, X=H$^-$ (hydride) and Y=BH$_4^-$, can be obtained according to the method described in J. Am. Chem. Soc. 2005, 127, 516, for example. Such complex is relatively stable, and therefore can be easily handled.

Examples of the preferred complex include a complex that is represented by the following Formula (8)

(in the Formula, (L) represents the tridentate aminodiphosphine represented by the above Formula (5)), and this complex is easily prepared by stirring the tridentate aminodiphosphine ligand L represented by the Formula (5) and RuClH (CO)(PPh$_3$)$_3$ in a suitable solvent.

Further, examples of the preferred complex include a complex represented by the following Formula (9)

(in the Formula, (L) represents the tridentate aminodiphosphine represented by the above Formula (5)), and this complex is easily prepared by stirring the ruthenium carbonyl complex represented by the Formula (8) and NaBH$_4$ in a suitable solvent.

By using the ruthenium carbonyl complex as a catalyst, it becomes possible to produce alcohols from esters, lactones, and ketones with high yield and high catalytic efficiency under relatively low hydrogen pressure and reaction temperature which are industrially advantageous.

In the present invention, esters, lactones, or ketones are used as a substrate for hydrogenation of reacting materials. However, the esters, lactones, or ketones may have a substituent group which does not exhibit any adverse effect on the hydrogenation method of the invention.

The method for producing alcohols by hydrogenation-reduction of ketones according to the invention is a method that is represented by the following reaction scheme (10), that is carried out by using the ruthenium carbonyl complex represented by the Formula (1) and a hydrogen donor.

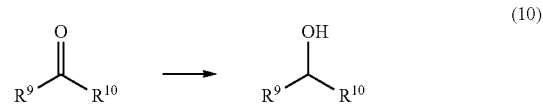

(in the scheme, R$^9$ and R$^{10}$, which may be the same or different from each other, represent a hydrogen atom, an alkyl group, a cycloalkyl group, an aryl group, an aralkyl group, a heterocyclic group, an alkenyl group, an alkynyl group, a cycloalkenyl group, or a keto group that is represented by the following Formula (I). Further, R$^9$ and R$^{10}$ may bind to each other to form a ring with an adjacent carbon atom. Further, the alkyl group, cycloalkyl group, aryl group, aralkyl group, heterocyclic group, alkenyl group, alkynyl group, and cycloalkenyl group may have a substituent group).

R$^9$ and R$^{10}$ in the reaction scheme (10) will be explained. Examples of the alkyl group, cycloalkyl group, aryl group, aralkyl group, and heterocyclic group include an alkyl group, a cycloalkyl group, an aryl group, an aralkyl group, and a heterocyclic group which are the same as those described with regard to R$^1$, R$^2$, R$^3$ and R$^4$ of the above Formula (2). Further, the alkenyl group may be linear or branched, and examples include an alkenyl group having 2 to 20 carbon atoms, preferably 2 to 15 carbon atoms, and more preferably 2 to 10 carbon atoms. Specific examples include an ethenyl group, a propenyl group, a 1-butenyl group, a pentenyl group, a hexenyl group, a heptenyl group, an octenyl group, a nonenyl group, and a decenyl group. Examples of the alkynyl group include a linear or branched alkynyl group which contains 2 to 20 carbon atoms, preferably 2 to 15 carbon atoms, and more preferably 2 to 10 carbon atoms. Specific examples include an ethynyl group, a 1-propynyl group, a 2-propynyl group, a 1-butynyl group, a 3-butynyl group, a pentynyl group, and a hexynyl group. Examples of the cycloalkenyl group include a 4 to 10-membered mono- to tricyclic aliphatic hydrocarbon group having 1 or 2 double bonds in the ring. Specific examples include a cyclobutenyl group, a cyclopentenyl group, a cyclohexenyl group, a cycloheptenyl group, or a cyclooctenyl group.

Examples of the keto group include those represented by the following Formula (I)

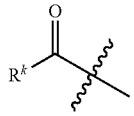

(I)

(in the Formula (I), $R^k$ represents a hydrogen atom, an alkyl group, a cycloalkyl group, an aryl group, an aralkyl group, a heterocyclic group, an alkenyl group, an alkynyl group, or a cycloalkenyl group. Further, the alkyl group, cycloalkyl group, aryl group, aralkyl group, heterocyclic group, alkenyl group, alkynyl group, and cycloalkenyl group may have a substituent group).

The alkyl group, cycloalkyl group, aryl group, aralkyl group, heterocyclic group, alkenyl group, alkynyl group, and cycloalkenyl group for $R^k$ are the same as those described above.

Further, examples of the substituent group which may be included in $R^9$, $R^{10}$ in the reaction scheme (10), and $R^k$ in the keto group include an alkyl group, a cycloalkyl group, an aryl group, an aralkyl group, an alkyloxy group, a cycloalkyloxy group, an aryloxy group, an aralkyloxy group, and a heterocyclic group, and a halogen atom, a silyl group, an amino group which is optionally protected, a hydroxy group which is optionally protected, which are the same as those described with regard to $R^1$, $R^2$, $R^2$ and $R^4$ of the Formula (2), or an alkenyl group, an alkynyl group, a cycloalkenyl group, and a keto group which are the same as those described for $R^9$ and $R^{10}$ in the reaction scheme (10).

When $R^9$ and $R^{10}$ are a keto group or have a keto group as a substituent group, polyhydric alcohol is obtained as a product.

When the reaction represented by the reaction scheme (10) is carried out by using a ruthenium carbonyl complex represented by the Formula (1) in which $R^9$ and $R^{10}$ are different from each other and the tridentate aminodiphosphine ligand represented by the Formula (2) or (3) is an optically active substance, an alcohol with one enantiomer present in excess is obtained as a product.

A method for producing alcohols by hydrogenation-reduction of esters or lactones according to the invention will be explained.

The method for producing alcohols by hydrogenation-reduction of esters according to the invention is a method that is carried out by using the ruthenium carbonyl complex represented by the Formula (1) and a hydrogen donor, in which alcohols are produced from esters according to the following reaction scheme (11)

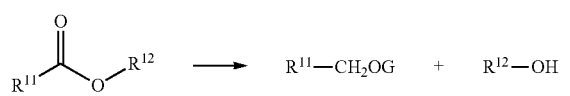

(11)

(in the scheme, $R^{11}$ and $R^{12}$, which may be the same or different from each other, represents an alkyl group, a cycloalkyl group, an aryl group, an aralkyl group, a heterocyclic group, an alkenyl group, an alkynyl group, a cycloalkenyl group, or a keto group that is represented by the above Formula (I), provided that $R^{11}$ may be a hydrogen atom.

Further, the alkyl group, cycloalkyl group, aryl group, aralkyl group, heterocyclic group, alkenyl group, alkynyl group, and cycloalkenyl group may have a substituent group).

The method for producing alcohols by hydrogenation-reduction of lactones according to the invention is a method that is carried out by using the ruthenium carbonyl complex represented by the Formula (1) and a hydrogen donor, in which the method is represented by the following reaction scheme (12)

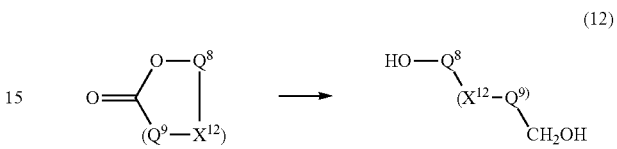

(12)

(in the scheme, $Q^8$ represents a divalent alkylene group, a divalent cycloalkylene group, a divalent aralkylene group, or a divalent arylene group, $(Q^9\text{-}X^{12})$ represents a bonding arm, or a group in which $Q^9$ is a divalent alkylene group, a divalent cycloalkylene group, a divalent aralkylene group, or a divalent arylene group and $X^{12}$ is a heteroatom such as oxygen, nitrogen, and sulfur. Further, the divalent alkylene group, divalent cycloalkylene group, divalent aralkylene group, or divalent arylene group in $Q^8$ and $Q^9$, and $X^{12}$ as a nitrogen atom may have a substituent group).

Explanations, will be given to $R^{11}$ and $R^{12}$ in the reaction scheme (11). Examples of the alkyl group, cycloalkyl group, aryl group, aralkyl group, and heterocyclic group expressed as $R^{11}$ and $R^{12}$ include an alkyl group, a cycloalkyl group, an aryl group, an aralkyl group, and a heterocyclic group which are the same as those described with regard to $R^1$, $R^2$, $R^3$ and $R^4$ of the above Formula (2). Further, examples of the alkenyl group, alkynyl group, cycloalkenyl group, and keto group include an alkenyl group, an alkynyl group, a cycloalkenyl group, and a keto group which are the same as those described with regard to $R^9$ and $R^{10}$ in the above reaction scheme (10).

Examples of the substituent group which may be included in $R^{11}$ and $R^{12}$ in the reaction scheme (11) include an alkyl group, a cycloalkyl group, an aryl group, an aralkyl group, an alkyloxy group, a cycloalkyloxy group, an aryloxy group, an aralkyloxy group, a halogen atom, a silyl group, a heterocyclic group, an amino group which is optionally protected, and a hydroxy group which is optionally protected, which are the same as those described with regard to $R^1$, $R^2$, $R^3$ and $R^4$ of the above Formula (2), or an alkenyl group, an alkynyl group, a cycloalkenyl group, and a keto group, an alkoxycarbonyl group, a cycloalkyloxycarbonyl group, an aryloxycarbonyl group, an aralkyloxycarbonyl group, an alkenyloxy group, an alkynyloxy group, and a cycloalkynyloxy group, which are the same as those described for $R^9$ and $R^{10}$ in the reaction scheme (10). However, when the protecting group for the hydroxy group which is optionally protected is an acyl group, a product with a reduced protecting group can be obtained. In addition, when $R^{11}$ and $R^{12}$ are a keto group, or when a keto group, an alkoxycarbonyl group, a cycloalkyloxycarbonyl group, an aryloxycarbonyl group, an aralkyloxycarbonyl group, an alkenyloxycarbonyl group, an alkynyloxycarbonyl group, or a cycloalkynyloxycarbonyl group is present as a substituent group, polyhydric alcohols in which these groups are hydrogenated and reduced can be obtained depending on the situation.

Examples of the alkoxycarbonyl group, cycloalkyloxycarbonyl group, aryloxycarbonyl group, aralkyloxycarbonyl group, alkenyloxycarbonyl group, alkynyloxycarbonyl group, and cycloalkynyloxycarbonyl group as a substituent group include those that are represented by the following Formula (13)

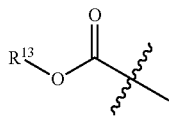

(13)

(in the Formula (13), $R^{13}$ represents an alkyl group, a cycloalkyl group, an aryl group, an aralkyl group, a heterocyclic group, an alkenyl group, an alkynyl group, or a cycloalkenyl group. Further, the alkyl group, cycloalkyl group, aryl group, aralkyl group, heterocyclic group, alkenyl group, alkynyl group, and cycloalkenyl group may have a substituent group).

Explanations will be given to $R^{13}$ of the Formula (13). Examples of the alkyl group, cycloalkyl group, aryl group, aralkyl group, and heterocyclic group include an alkyl group, a cycloalkyl group, an aryl group, an aralkyl group, and a heterocyclic group which are the same as those described with regard to $R^1$, $R^2$, $R^3$ and $R^4$ of the above Formula (2). Further, examples of the alkenyl group, alkynyl group, and cycloalkenyl group include an alkenyl group, an alkynyl group, and a cycloalkenyl group which are the same as those described with regard to $R^9$ and $R^{10}$ in the reaction scheme (10).

Examples of the substituent group which may be included in $R^{13}$ of the Formula (13) include an alkyl group, a cycloalkyl group, an aryl group, an aralkyl group, and a heterocyclic group which are the same as those described with regard to $R^1$, $R^2$, $R^3$ and $R^4$ of the above Formula (2) and an alkenyl group, an alkynyl group, and a cycloalkenyl group which are the same as those described with regard to $R^9$ and $R^{10}$ in the reaction scheme (10).

Preferred examples of $R^{12}$ include an alkyl group having 1 to 10 carbon atoms. Specific examples include a methyl group, an ethyl group, and an isopropyl group. More preferably, it is a methyl group.

Explanations will be given to $Q^8$ and $Q^9$ in the reaction scheme (12). Examples of the divalent alkylene group, divalent cycloalkylene group, and divalent aralkylene group that are represented by $Q^8$ and $Q^9$ include a divalent alkylene group, a divalent cycloalkylene group, and a divalent aralkylene group which are the same as those described with regard to $Q^1$ and $Q^2$ of the above Formula (2). Examples of the divalent arylene group include a divalent group made of a monocyclic or condensed-cyclic aryl group having 6 to 12 carbon atoms such as phenylene group and 2,3-naphthalenediyl group. Examples, of the phenylene group include o- or m-phenylene group.

Examples of the substituent group which may be included in $Q^8$ and $Q^9$ in the reaction scheme (12) include an alkyl group, a cycloalkyl group, an aryl group, an aralkyl group, an alkyloxy group, a cycloalkyloxy group, an aryloxy group, an aralkyloxy group, a halogen atom, a silyl group, a heterocyclic group, an amino group which is optionally protected, a hydroxy group which is optionally protected, which are the same as those described with regard to $R^1$, $R^2$, $R^3$ and $R^4$ of the above Formula (2), or an alkenyl group, an alkynyl group, a cycloalkenyl group, an alkoxycarbonyl group, a cycloalkyloxycarbonyl group, an aryloxycarbonyl group, an aralkyloxycarbonyl group, an alkenyloxy group, an alkynyloxy group, and a cycloalkynyloxy group, which are the same as those described with regard to $R^9$ and $R^{10}$ in the reaction scheme (10). However, when the protecting group for the hydroxy group which is optionally protected is an acyl group, a product with a reduced protecting group can be obtained. In addition, when an alkoxycarbonyl group, cycloalkyloxycarbonyl group, an aryloxycarbonyl group, an aralkyloxycarbonyl group, an alkenyloxycarbonyl group, an alkynyloxycarbonyl group, or a cycloalkynyloxycarbonyl group is included as a substituent group, polyhydric alcohols in which these groups are hydrogenated and reduced may be obtained. Further, examples of the substituent group which may be provided with the nitrogen atom when the heteroatom represented by $X^{12}$ is a nitrogen atom include an alkyl group, a cycloalkyl group, an aryl group, and an aralkyl group which are the same as those described with regard to $R^1$, $R^2$, $R^3$ and $R^4$ of the Formula (2), and a general protecting group for amino group as described in the above Reference 1.

Examples of the preferred lactones include β-lactone, γ-lactone, and δ-lactone.

According to the hydrogenation-reduction of optically active esters or lactones in which $R^{11}$, $Q^8$, or $Q^9$ is a group having a chiral center by following the method of the invention, alcohols with the original stereochemistry of the esters or lactones maintained can be obtained without having a significant reduction in optical purity.

The method for producing alcohols of the invention may be appropriately carried out in the presence or absence of a solvent. However, it is preferable to use a solvent. Preferably, the solvent to be used can dissolve the substrate and catalyst, and it is used either singly or as a mixture of the solvents. Specific examples of the solvent include an aromatic hydrocarbon such as toluene and xylene, an aliphatic hydrocarbon such as hexane and heptane, a halogenated hydrocarbon such as methylene chloride and chlorobenzene, ethers such as diethyl ether, tetrahydrofuran, methyl tert-butyl ether, and cyclopentyl methyl ether, alcohols such as methanol, ethanol, isopropanol, n-butanol, 2-butanol, and tert-butanol, and polyhydric alcohols such as ethylene glycol, propylene glycol, 1,2-propane diol, and glycerin. Among them, ethers or alcohols are preferable, and examples of a particularly preferred solvent include tetrahydrofuran, methanol, or isopropanol. The amount of the solvent to be used can be appropriately selected depending on the reaction condition, etc. If necessary, the reaction is carried out under stirring.

Examples of the hydrogen donor that is used for the method of the invention include molecular hydrogen, formic acid, primary alcohol (methanol, ethanol, and butanol, etc.), and secondary alcohol (isopropanol, etc.). Preferred examples include molecular hydrogen and secondary alcohol.

The amount of the catalyst to be used varies depending on the substrate to be hydrogenated, reaction condition, and type of the catalyst, etc. However, in terms of the molar ratio of the ruthenium complex to the substrate to be hydrogenated, it is generally within the range of 0.0001 mol % to 10 mol %, and preferably 0.005 mol % to 5 mol %. According to the method of the invention, the reaction temperature for carrying out the hydrogenation-reduction is 0° C. to 180° C., and preferably 0° C. to 120° C. If the reaction temperature is too low, a large amount of raw materials may remain as unreacted material. On the other hand, if the temperature is too high, decomposition of the raw materials and catalyst, etc. may occur, which is undesirable. According to the invention, the hydrogen pressure for carrying out the hydrogenation-reduction is 0.1 MPa to 10 MPa, and preferably 3 MPa to 6 MPa. Further, with the reaction time of 30 min to 72 hrs, and preferably 2 hrs to 48 hrs, sufficient high conversion rate of the raw materials can be obtained.

After the completion of the reaction, the desired alcohols can be obtained by following a purification method that is generally used such as extraction, filtration, crystallization, distillation, and various chromatographies, etc., either singly or in combination thereof.

The hydrogenation-reduction of the invention may be carried out with addition of an appropriate additive.

Examples of the additive include a basic compound or a metal hydride, etc. Specific examples of the basic compound include amines such as triethylamine, diisopropylethylamine, N,N-dimethylaniline, piperidine, pyridine, 4-dimethylaminopyridine, 1,5-diazabicyclo[4.3.0]nona-5-ene, 1,8-diazabicyclo[5.4.0]undec-7-ene, tri-n-butylamine, and N-methylmorpholine, alkali metal carbonates such as potassium carbonate, sodium carbonate, lithium carbonate, and cesium carbonate, alkali earth metal carbonates such as magnesium carbonate and calcium carbonate, alkali metal hydrogen carbonates such as sodium hydrogen carbonate and potassium hydrogen carbonate, alkali metal hydroxides such as sodium hydroxide, potassium hydroxide, and lithium hydroxide, alkali earth metal hydroxides such as magnesium hydroxide and calcium hydroxide, alkali metal alkoxides such as sodium methoxide, sodium ethoxide, sodium isopropoxide, sodium tert-butoxide, potassium methoxide, potassium ethoxide, potassium isopropoxide, potassium tert-butoxide, lithium methoxide, lithium isopropoxide, and lithium tert-butoxide, alkali earth metal alkoxides such as magnesium methoxide and magnesium ethoxide, and metal hydrides such as sodium hydride and calcium hydride. Examples of a particularly preferred base include sodium methoxide or potassium tert-butoxide.

Examples of the metal hydride include lithium borohydride, sodium borohydride, potassium borohydride, and lithium aluminum hydride. These metal hydrides can yield sufficient high conversion rate even when they are used in an amount of 10 mol % of the esters or less, lactones, or ketones which are the substrate to be hydrogenated.

EXAMPLES

The present invention is hereinafter explained in more detail by means of the following Examples, to which, however, the invention is never limited.

Further, measurement of conversion rate, selectivity, and optical purity was performed by gas chromatography (GC) and liquid chromatography (LC). The instruments used are as follows.

Conversion Rate Selectivity

For the analysis of the conversion rate and the selectivity, condition A, B, C, or D was employed.

Analysis condition A:
GC; capillary HP-INNOWax
Injection temperature 250° C., detection temperature 250° C. 80° C. (1 min.)–10° C./min–250° C. (12 min.)

Analysis condition B:
GC; capillary RTx-5
Injection temperature 250° C., detection temperature 250° C. 80° C. (10 min.)–10° C./min–270° C. (1 min.)

Analysis condition C:
GC; capillary TC-WAX
Injection temperature 250° C., detection temperature 250° C. 80° C.–10° C./min–200° C. (2 min.)

Analysis condition D:
GC; capillary CP-CHIRASIL-DEX-CB
Injection temperature 250° C., detection temperature 250° C. 115° C. (12 min.)

The optical purity of the each product was determined according to the following methods.

Optical purity: optical purity analysis of 1,2-propane diol
Analysis was carried out after conversion into propylene carbonate.
GC; capillary β-DEX225
Injection temperature 250° C., detection temperature 250° C. 170° C. (30 min.)

Optical purity: optical purity analysis of 2-(Boc-amino) propan-1-ol
Analysis was carried out after conversion into p-nitrobenzoic acid ester.
HPLC; column DAICEL CHIRALCEL OD-H
Oven; 40° C., Eluent; hexane:isopropanol=95:5

Optical purity: optical purity analysis of 2-(benzyloxy) propan-1-ol
HPLC; column DAICEL CHIRALCEL AD-H
Oven; 30° C., Eluent; hexane:isopropanol=98:2

Optical purity: optical purity analysis of 3-(Boc-amino) butan-1-ol
Analysis was carried out after conversion into p-nitrobenzoic acid ester.
HPLC; column DAICEL CHIRALCEL AD-H
Oven; 30° C., Eluent; hexane:isopropanol=90:10

Optical purity: optical purity analysis of 3-(phenylamino) butan-1-ol
HPLC; column DAICEL CHIRALCEL AS-H
Oven; 30° C., Eluent; hexane:isopropanol=95:5

Optical purity: optical purity analysis of 3-(tert-butyldimethylsilyloxy)butan-1-ol
GC; capillary CP-CHIRASIL-DEX-CB
Injection temperature 250° C., detection temperature 250° C. 80° C. (30 min.)

Optical purity: optical purity analysis of 1-phenylethanol
GC; capillary CP-CHIRASIL-DEX-CB
Injection temperature 250° C., detection temperature 250° C. 115° C. (12 min.)

For the measurement of $^1$H-NMR spectrum and $^{31}$P-NMR spectrum, MERCURY plus 300 manufactured by Varian, Inc. was used.

Example 1

According to the following reaction scheme, the ruthenium carbonyl complex 1a and 1b were produced.

-continued

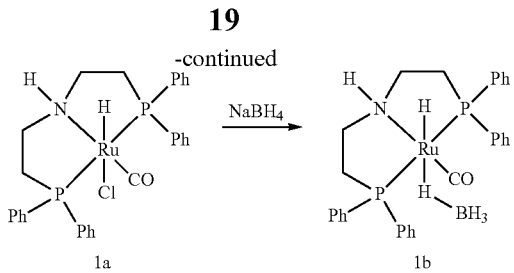

Under a nitrogen stream, the amine hydrochloride 8 (4.18 mmol) was added to a 100 mL flask and suspended in toluene (33 mL). After adding 15% aqueous NaOH solution (14 mL), it was stirred at room temperature until the solids disappear. After the fractionation of the solution, the organic layer was washed with distilled water (14 mL×2) and the aqueous layer was extracted with toluene (14 mL×2). The combined organic layer was dried over sodium sulfate and the solvent was removed by distillation to obtain the amine 9.

The ruthenium carbonyl complex 7 (4.18 mmol) was added to a 200 mL flask, purged with nitrogen gas, and added with the amine 9 dissolved in toluene (33 mL). The mixture was refluxed with heating for 60 min. After cooling, hexane (82 mL) was added to the reaction solution and the crystals precipitated under the nitrogen atmosphere were filtered. The crystals thus obtained were washed with hexane (10 mL) and ethanol (40 mL). After drying under reduced pressure, 1.4 g (2.3 mmol) of the ruthenium complex 1a was obtained.

$^1$H-NMR (300 MHz $CD_2Cl_2$): δ=−15.23 (t, J=29.3 Hz, 1H), 2.40-2.65 (m, 4H), 2.90-3.05 (m, 2H), 3.30-3.55 (m, 2H), 3.92 (bs, 1H),
7.08-7.34 (m, 4H), 7.38-7.46 (m, 8H), 7.40-7.88 (m, 8H)
$^{31}$P-NMR (121.5 MHz $CD_2Cl_2$): δ=52.8 (d, J=14 Hz)

Under a nitrogen stream, the complex 1a (2.22 mmol) produced above was added to a 1000 mL flask and suspended in toluene (222 mL). After adding $NaBH_4$ (60.0 mmol) dissolved in ethanol (222 mL) thereto, the suspension was stirred at 65° C. for 30 min and at room temperature for 30 min. The solvent was then distilled off under reduced pressure. Hexane (220 mL) and distilled water (110 mL) were added to the residue. After stirring for 15 min, the precipitated crystals were filtered. The crystals thus obtained were washed with distilled water (110 mL×2) and hexane (110 mL×2). After drying under reduced pressure, 1.05 g (1.79 mmol) of the target ruthenium complex 1b was obtained.

$^1$H-NMR (300 MHz $CD_2Cl_2$): δ=−12.36 (t, J=28.5 Hz, 1H), −2.80-1.70 (bs, 4H), 2.40-2.78 (m, 4H), 2.90-3.05 (m, 2H), 3.32-3.60 (m, 2H), 4.20-4.40 (m, 1H), 6.92-7.28 (m, 4H), 7.38-7.46 (m, 8H), 7.70-7.82 (m, 8H)
$^{31}$P-NMR (121.5 MHz $CD_2Cl_2$): δ=56.6 (s)

Example 2

Hydrogenation of methyl(R)-lactate was carried out according to the following reaction scheme.

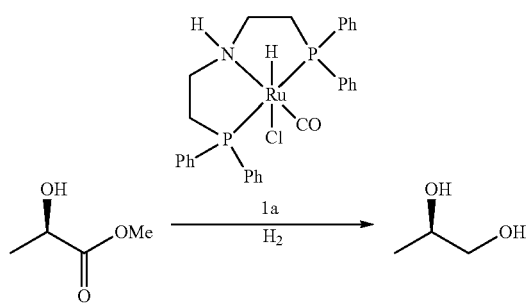

A solution of methyl(R)-lactate (10 mmol) having optical purity of 99.3% ee, the complex 1a (0.01 mmol) produced in Example 1, methanol (7.6 mL), and 0.5 M of sodium methoxide in methanol (0.4 mL) was added to a 100 mL autoclave equipped with a stirrer, and the hydrogenation-reduction was carried out at 30° C. for 16 hrs with hydrogen pressure of 5 MPa. As a result of the analysis of the reaction solution according to gas chromatography, the conversion rate was 96.3%. Optical purity of the alcohol obtained was 99.1% ee.

Example 3

Hydrogenation of methyl L-Boc-alanine ester was carried out according to the following reaction scheme.

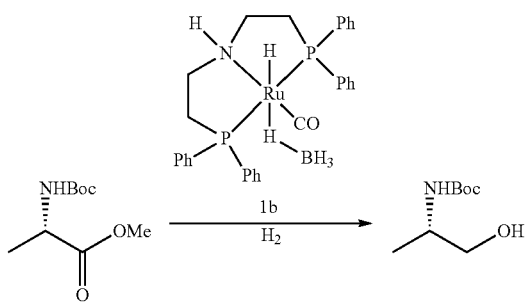

Methyl L-Boc-alanine ester (5 mmol), the complex 1b (0.01 mmol) produced in Example 1, and tetrahydrofuran (4 mL) were added to a 100 mL autoclave equipped with a stirrer, and the hydrogenation was carried out at 80° C. for 16 hrs with hydrogen pressure of 5 MPa. As a result of the analysis of the reaction solution according to gas chromatography, it was found that (S)-2-(Boc-amino)propan-1-ol was produced with the conversion rate of 100% and the selectivity of 100%. Optical purity of the alcohol obtained was 99% ee or higher.

Example 4

Hydrogenation of methyl(S)-2-(benzyloxy)propionate was carried out according to the following reaction scheme.

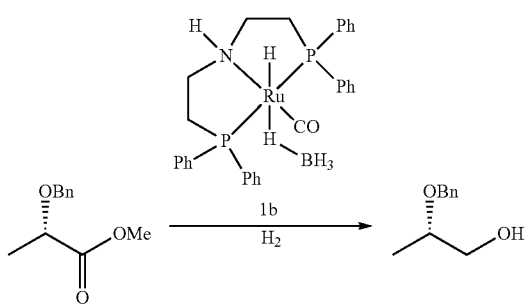

Methyl(S)-2-(benzyloxy)propionate (5 mmol) with optical purity of 98.5% ee, the complex 1b (0.01 mmol) produced in Example 1, and tetrahydrofuran (4 mL) were added to a 100 mL autoclave equipped with a stirrer, and the hydrogenation was carried out at 80° C. for 16 hrs with hydrogen pressure of 5 MPa. As a result of the analysis of the reaction solution according to gas chromatography, it was found that (S)-2-(benzyloxy)propan-1-ol was obtained with the conversion rate of 100% and the selectivity of 99%. Optical purity of the alcohol obtained was 98.5% ee.

Example 5

Hydrogenation of methyl(R)-3-(Boc-amino)butanoate was carried out according to the following reaction scheme.

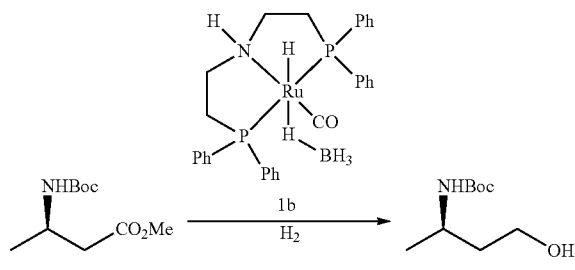

The complex 1b (0.02 mmol) produced in Example 1 was added to a 100 mL autoclave equipped with a stirrer and purged with nitrogen gas. Tetrahydrofuran (4 mL) and methyl (R)-3-(Boc-amino)butanoate (5 mmol) with 99% ee or higher were added thereto, and the hydrogenation was carried out at 80° C. for 16 hrs with hydrogen pressure of 5 MPa. As a result of the analysis of the reaction solution according to gas chromatography, it was found that (R)-3-(Boc-amino)butan-1-ol was obtained with the conversion rate of 95.9%. Optical purity of the alcohol obtained was 99% ee or higher.

Example 6

Hydrogenation of methyl(S)-3-(phenylamino)butanoate was carried out according to the following reaction scheme.

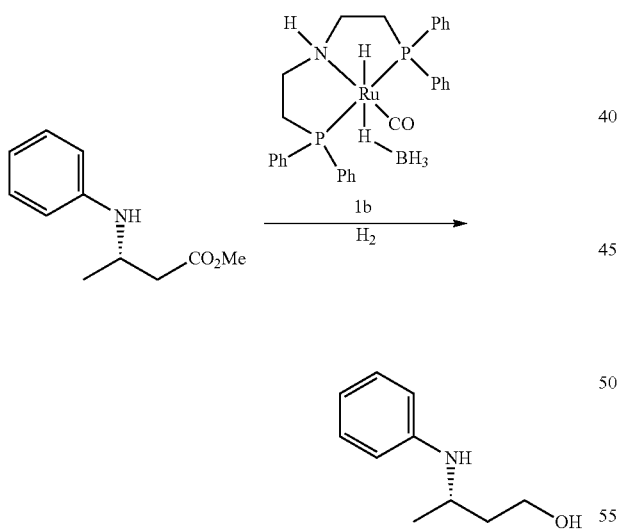

Methyl(S)-3-(phenylamino) butanoate (5 mmol) with optical purity of 93.9% ee, the complex 1b (0.01 mmol) produced in Example 1, and tetrahydrofuran (4 mL) were added to a 100 mL autoclave equipped with a stirrer, and the hydrogenation was carried out at 80° C. for 16 hrs with hydrogen pressure of 5 MPa. As a result of the analysis of the reaction solution according to gas chromatography, it was found that (3S)-3-(phenylamino)butan-1-ol was obtained with the conversion rate of 86.4%. Optical purity of the alcohol obtained was 91.1% ee.

Example 7

Hydrogenation of methyl (R)-3-(tert-butyldimethylsilyloxy)butanoate was carried out according to the following reaction scheme.

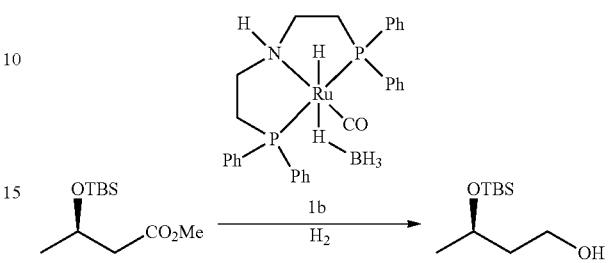

Methyl (3R)-3-tert-butyldimethylsilyloxy butanoate (5.0 mmol) with optical purity of 99% ee, the complex 1b (0.02 mmol) produced in Example 1, and tetrahydrofuran (4 mL) were added to a 100 mL autoclave equipped with a stirrer, and the hydrogenation was carried out at 80° C. for 16 hrs with hydrogen pressure of 5 MPa. As a result of the analysis of the reaction solution according to gas chromatography, it was found that (R)-3-(tert-butyldimethylsilyloxy)butan-1-ol was obtained with the reaction conversion rate of 87.9%. Optical purity of the alcohol obtained was 99% ee.

Example 8

Hydrogenation of methyl benzoate was carried out according to the following reaction scheme.

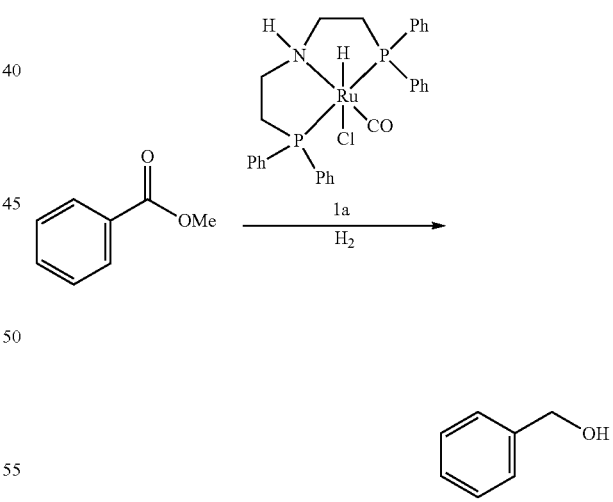

Methyl benzoate (10.0 mmol), the complex 1a (0.01 mmol) produced in Example 1, sodium methoxide (0.5 mmol), and tetrahydrofuran (5 mL) were added to a 100 mL autoclave equipped with a stirrer, and the hydrogenation was carried out at 80° C. for 13.5 hrs with hydrogen pressure of 5 MPa. As a result of the analysis of the reaction for the reaction solution according to gas chromatography, it was found that benzyl alcohol was obtained with the reaction conversion rate of 96%.

Example 9

Hydrogen-transfer type reduction of isopropyl benzoate was carried out according to the following reaction scheme.

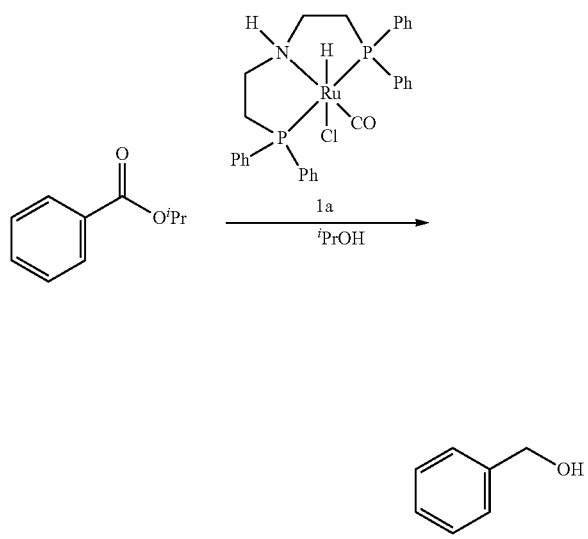

Isopropyl benzoate (6.15 mmol), the complex 1a (0.06 mmol) produced in Example 1, and 0.1 M of potassium tert-butoxide solution in isopropanol (12.3 mL), and isopropanol (8 mL) were added to a 100 mL autoclave equipped with a stirrer, and then stirred at 80° C. for 16 hrs. As a result of the analysis of the reaction for the reaction solution according to gas chromatography, it was found that benzyl alcohol was obtained with the reaction conversion rate of 21.0% and selectivity of 47.0%.

Example 10

Hydrogenation of acetophenone was carried out according to the following reaction scheme.

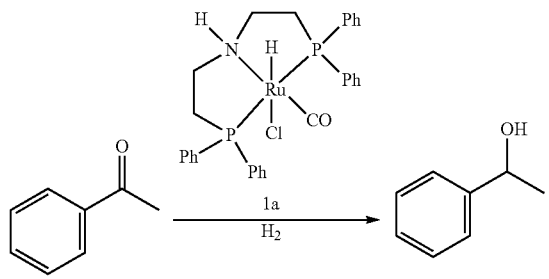

Acetophenone (20.1 mmol), the complex 1a (0.01 mmol) produced in Example 1, potassium tert-butoxide (0.1 mmol), and isopropanol (11.5 mL) were added to a 100 mL autoclave equipped with a stirrer, and the hydrogenation was carried out at 40° C. for 17.5 hrs with hydrogen pressure of 3 MPa. As a result of the analysis of the reaction for the reaction solution according to gas chromatography, it was found that 1-phenylethanol was produced with the reaction conversion rate of 100%.

Example 11

Asymmetric hydrogenation of acetophenone was carried out according to the following reaction scheme by using the ruthenium carbonyl complex containing an optically active tridentate aminodiphosphine ligand.

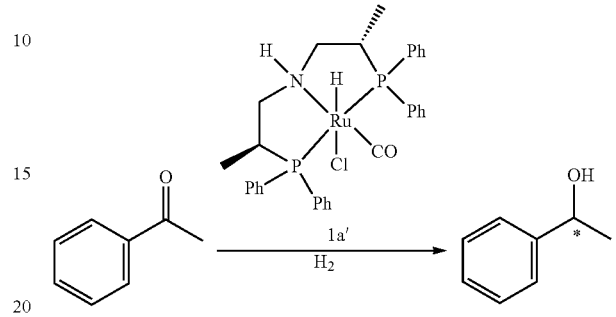

(1) Production of Ruthenium Carbonyl Complex Containing Optically Active Tridentate Aminodiphosphine Ligand The desired ruthenium carbonyl complex 1a' containing an optically active tridentate aminodiphosphine ligand was produced in the same manner as Example 1 except that, as a tridentate aminodiphosphine ligand, N,N-bis[(S)-2-diphenylphosphino-propyl]amine was used instead of the amine 9 described in Example 1.

(2) Asymmetric Hydrogenation of Acetophenone

Acetophenone (20 mmol), the complex 1a' (0.01 mmol) containing an optically active ligand, potassium tert-butoxide (0.1 mmol), and isopropanol (11.5 mL) were added to a 100 mL autoclave equipped with a stirrer, and the hydrogenation was carried out at 40° C. for 5 hrs with hydrogen pressure of 3 MPa. As a result of the analysis of the reaction for the reaction solution according to gas chromatography, it was found that 1-phenylethanol was obtained with the reaction conversion rate of 100%. Optical purity of the alcohol thus obtained was 54.0% ee.

Example 12

Hydrogen-transfer type asymmetric reduction of acetophenone was carried out according to the following reaction scheme.

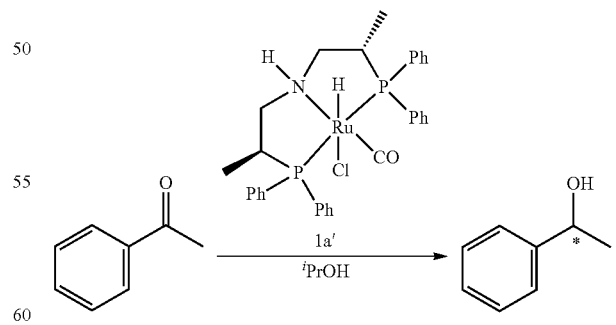

Acetophenone (20 mmol), the complex (0.01 mmol) 1a' containing an optically active ligand that is produced in Example 11, 0.1 M of solution of potassium tert-butoxide in isopropanol (1 mL), and isopropanol (10.5 mL) were added to a 20 mL flask equipped with a stirrer, and the mixture was stirred at 40° C. for 8.5 hrs under a nitrogen stream. As a result of the analysis of the reaction solution according to gas chromatography, it was found that 1-phenylethanol was obtained with the reaction conversion rate of 72%. Optical purity of the alcohol thus obtained was 40.0% ee.

Example 13

Hydrogenation of methyl(R)-lactate was carried out according to the following reaction scheme.

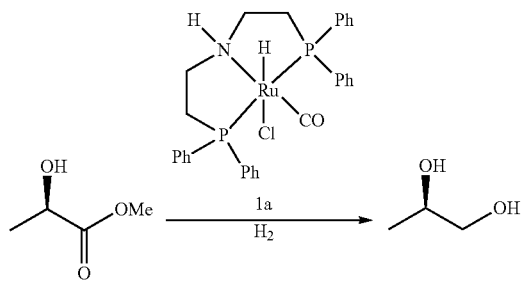

Methyl(R)-lactate (50 mmol), the complex 1a (0.01 mmol) produced in Example 1, sodium methoxide (0.5 mmol), and tetrahydrofuran (19 mL) were added to a 100 mL autoclave equipped with a stirrer, and the hydrogenation was carried out at 80° C. for 16 hrs with hydrogen pressure of 5 MPa. As a result of the analysis of the reaction solution according to gas chromatography, it was found that the conversion rate was 95%.

Example 14

Hydrogenation of methyl(R)-lactate was carried out according to the following reaction scheme.

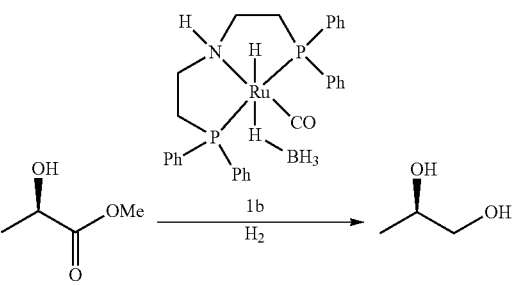

Methyl(R)-lactate (10 mmol) with optical purity of 99.3% ee, the complex 1b (0.01 mmol) produced in Example 1, and isopropanol (7.6 mL) were added to a 100 mL autoclave equipped with a stirrer, and the hydrogenation-reduction was carried out at 80° C. for 16 hrs with hydrogen pressure of 5 MPa. As a result of the analysis of the reaction solution according to gas chromatography, it was found that the conversion rate was 98.4%. Optical purity of the alcohol thus obtained was 81.8% ee.

Example 15

The reaction was performed in the same manner as Example 14 except that isopropanol was changed to toluene. As a result, the conversion rate was 88.2%. Optical purity of the alcohol thus obtained was 88.8% ee.

Example 16

The reaction was performed in the same manner as Example 14 except that isopropanol was changed to ethanol. As a result, the conversion rate was 98.3%. Optical purity of the alcohol thus obtained was 93.7% ee.

Example 17

The ruthenium carbonyl complex 14 of the invention was produced in accordance with the following procedure.

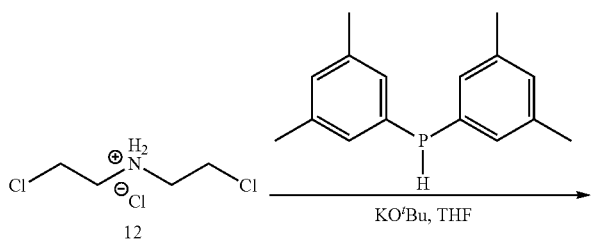

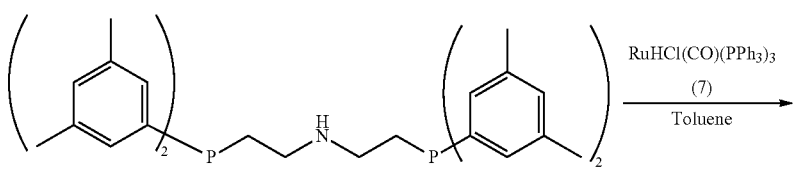

-continued

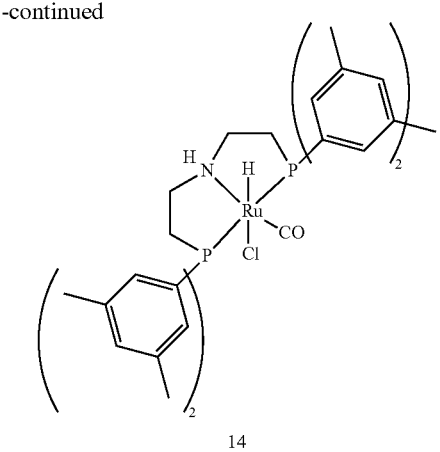

14

Under a nitrogen stream, potassium tert-butoxide (22.3 mmol) was added to a 100 mL flask and suspended in tetrahydrofuran (40 mL). Subsequently, after adding bis(3,5-dimethylphenyl)phosphine (11.0 mmol) and the amine 12 (5.5 mmol) thereto, the mixture was refluxed for 6 hrs, then stirred at 50° C. for 12 hrs and further refluxed for 2 hrs. After that, the reaction solution was diluted with ethyl acetate and washed with 15% aqueous NaOH solution and distilled water. The aqueous layer was extracted with diethyl ether. The combined organic layer was dried over magnesium sulfate and subjected to drying under reduced pressure to obtain a crude product, which was then purified by base-treated silica gel column chromatography to give 1.63 g (54%) of the bisphosphinoamine 13.

$^1$H-MNR (300 MHz CDCl$_3$): δ=2.27 (s, 24H), 2.19-2.34 (m, 4H), 2.68-2.80 (m, 4H), 6.93 (s, 4H), 7.02 (d, J=8.1 Hz, 8H)

$^{31}$P-NMR (121.5 MHz CDCl$_3$): δ=−22.89 (s)

Subsequently, under a nitrogen stream, the bisphosphinoamine 13 (0.72 mmol) was added to a 50 mL flask, added with toluene (8.5 mL) and the complex 7 (0.60 mmol), and then refluxed with heating for 5 hrs. After that, the reaction solution was purified by silica gel column chromatography to obtain the complex 14.

$^1$H-MNR (300 MHz CD$_2$Cl$_2$): δ=−15.37 (t, J=29.1 Hz, 1H), 2.34 (s, 12H), 2.36 (s, 12H), 2.40-2.50 (m, 4H), 2.80-3.20 (m, 2H), 3.30-3.50 (m, 2H), 3.75-3.95 (bs, 1H), 7.05-7.80 (m, 4H), 7.36-7.46 (m, 8H)

$^{31}$P-NMR (121.5 MHz CD$_2$Cl$_2$): δ=51.68 (d, J=11.7 Hz)

Example 18

Hydrogenation of methyl(R)-lactate was carried out.

Methyl lactate (20.0 mmol), the complex 14 (0.01 mmol) produced in Example 17, sodium methoxide (0.2 mmol), and methanol (8 mL) were added to a 100 mL autoclave equipped with a stirrer, and the hydrogenation was carried out at 30° C. for 16 hrs with hydrogen pressure of 5 MPa. As a result of the analysis of the reaction for the reaction solution according to gas chromatography, it was found that the conversion rate was 48% and the selectivity was 98%. Optical purity of the alcohol thus obtained was 99.1% ee.

Example 19

The ruthenium carbonyl complex 18 of the invention was produced in accordance with the following procedure.

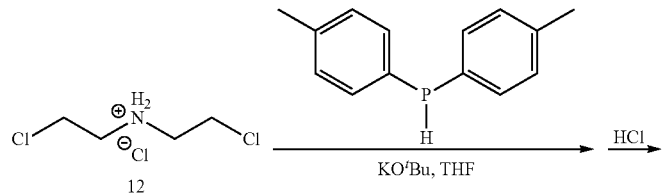

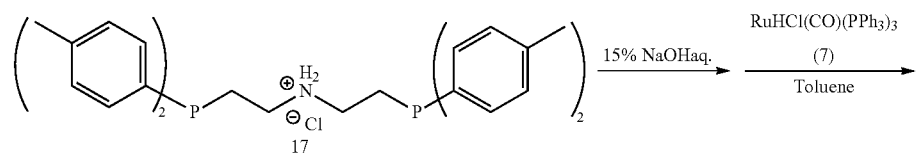

-continued

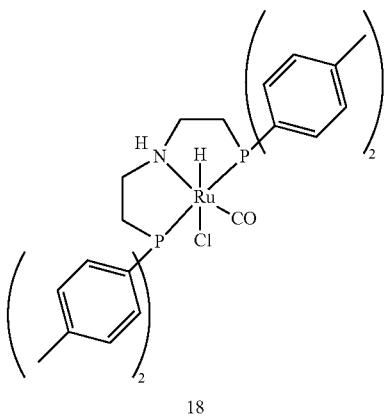

18

Under a nitrogen stream, potassium tert-butoxide (8.0 mmol) was added to a 100 mL flask and suspended in tetrahydrofuran (40 mL). After adding di(p-tolyl)phosphine (4.0 mmol) and the amine 12 (2.0 mmol) thereto, the mixture was reacted for 14 hrs at room temperature and refluxed with heating for 5 hrs. The reaction solution was then diluted with ethyl acetate (40 mL) and washed with 15% aqueous NaOH solution, distilled water, and saturated brine. The aqueous layer was extracted with ethyl acetate and the combined organic layer was dried over sodium sulfate and subjected to drying under reduced pressure. After that, hexane (40 mL) and 1 N HCl were added to the mixture, which was then reacted for 30 min at room temperature. The precipitated solids were filtered, washed with hexane, and dried under reduced pressure to obtain the amine hydrochloride 17 as a mixture.

Subsequently, under a nitrogen stream, the amine hydrochloride 17 (0.36 mmol) was added to a 20 mL flask and suspended in toluene (5.0 mL). After adding 15% aqueous NaOH solution thereto, the reaction was carried out at room temperature for 30 mm. After separating into two layers, the organic layer was washed with saturated brine and the aqueous layer was extracted with toluene (1 mL). The combined organic layer was prepared as a toluene solution of the amine. Under a nitrogen stream, the toluene solution of the amine just prepared and the complex 7 (0.30 mmol) were added to a 20 mL flask and refluxed with heating for 5 hrs. After that, the reaction solution was filtered and then recrystallized by adding hexane to the filtrate. The precipitated crystals were filtered and washed with toluene:hexane=1:1. Thereafter, the resultant was dried under reduced pressure to give the complex 18.

$^1$H-MNR (300 MHz CD$_2$Cl$_2$): δ=−15.35 (t, J=19.5 Hz, 1H), 2.36 (s, 12H), 2.42-2.52 (m, 4H), 2.88-3.00 (m, 2H), 3.30-3.52 (m, 2H), 3.74-3.88 (m, 1H), 7.18-7.27 (m, 8H), 7.60-7.40 (m, 8H)

$^{31}$P-NMR (121.5 MHz CD$_2$Cl$_2$): δ=50.93 (d, J=14.2 Hz)
MS: as C$_{33}$H$_{38}$ClNOP$_2$Ru,
Calculated value: (MH$^{30}$)=663.12
Measured value: (MH$^{30}$)=663.07

The complex 18 obtained from Example 19 was prepared as a monocrystal by using toluene-hexane, and the X ray structure analysis was carried out by using Rigaku Mercury CCD, Crystal Clear. The analysis was made by using SHELX97 of Crystal Structure 3.8.

The results of X ray structure analysis of the monocrystal are as follows.

Crystal system: monoclinic system.
Space group: P121/c1.
Lattice constant a=12.5423 (13), b=14.5907 (11), c=18.0776 (15)(unit is Å (angstrom)), β=102.131 (4), V=3234.3 (5) (Å$^3$ (cubic angstrom)).
The bond length around the Ru is as follows. 1.65 Å (angstrom) for Ru—H; 1.834 Å (angstrom) for Ru—C; 2.191 Å (angstrom) for Ru—N; 2.3358 Å (angstrom) and 2.3068 Å (angstrom) for Ru—P, respectively.
The schematic drawing of the chemical structure of the complex 18 according to the results above is shown in FIG. 1.

Example 20

Hydrogenation of methyl(R)-lactate was carried out.
Methyl lactate (10.0 mmol), the complex 18 (0.005 mmol) produced in Example 19, sodium methoxide (0.1 mmol), and methanol (4 mL) were added to a 100 mL autoclave equipped with a stirrer, and the hydrogenation was carried out at 30° C. for 16 hrs with hydrogen pressure of 5 MPa. As a result of the analysis of the reaction solution according to gas chromatography, it was found that the reaction conversion rate was 70% and the selectivity was 94%.

Example 21

The ruthenium carbonyl complex 16 was produced in accordance with the following procedure.

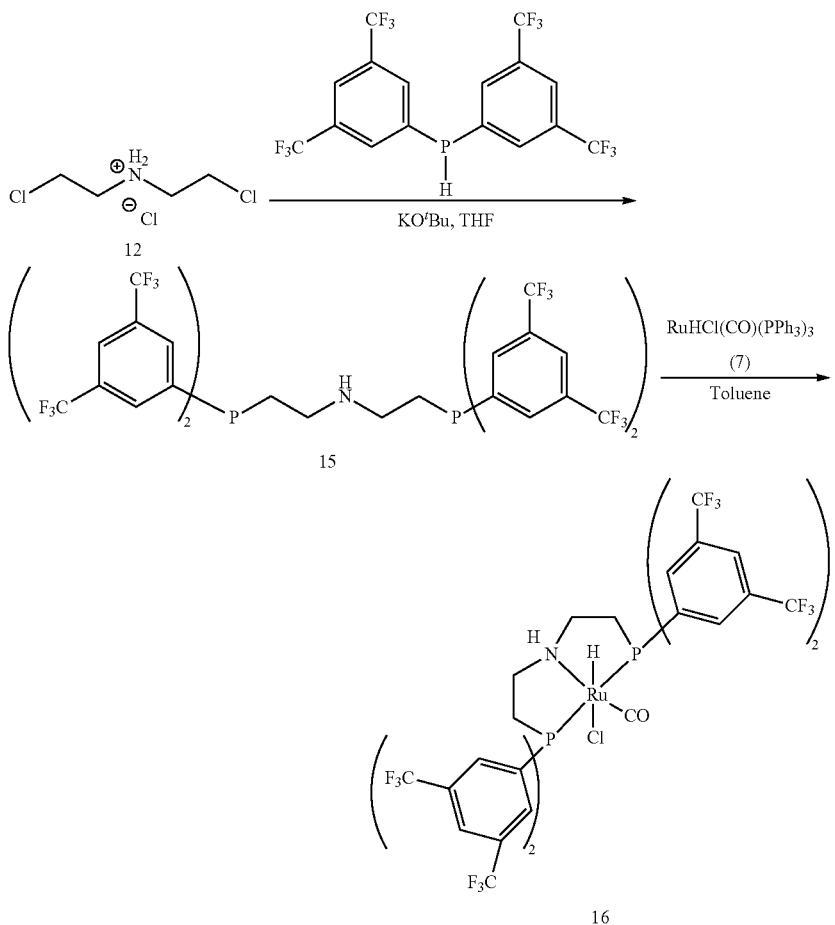

Under a nitrogen stream, potassium tert-butoxide (2.2 mmol) was added to a 20 mL flask and suspended in tetrahydrofuran (10 mL). After adding bis(3,5-bis(tri fluoromethyl)phenyl)phosphine (1.09 mmol) and the amine 12 (0.55 mmol) thereto, the mixture was refluxed with heating for 4 hrs. After that, the reaction solution was distilled off under reduced pressure, and the residues were added with ethyl acetate and washed with 15% aqueous NaOH solution and saturated brine. The obtained organic layer was dried over sodium sulfate and subjected to drying under reduced pressure to yield the amine 15 as a crude product.

$^{31}$P-NMR (121.5 MHz CDCl$_3$): δ=−14.67 (s)

Subsequently, under a nitrogen stream, the amine 15 (0.55 mmol) was added to a 50 mL flask and suspended in toluene (6.6 mL). After adding the complex 7 (0.46 mmol) thereto, the mixture was refluxed with heating for 4 hrs. After that, the reaction solution was cooled to room temperature, and the precipitated crystals were filtered. The crystals were washed with toluene and diethyl ether followed by drying under reduced pressure to obtain the complex 16.

$^1$H-MNR (300 MHz CD$_2$Cl$_2$): δ=−14.59 (t, J=18.6 Hz, 1H), 2.35-2.60 (m, 2H), 2.65-2.85 (m, 2H), 3.02-3.18 (m, 2H), 3.35-3.65 (m, 2H), 3.80-4.20 (m, 1H) 8.04 (d, J=21.6 Hz, 4H), 8.18-8.26 (m, 4H), 8.36-8.44 (m, 4H)

$^{31}$P-NMR (121.5 MHz CD$_2$Cl$_2$): δ=60.18 (s)

Example 22

Hydrogenation of methyl maleate was carried out according to the following reaction scheme.

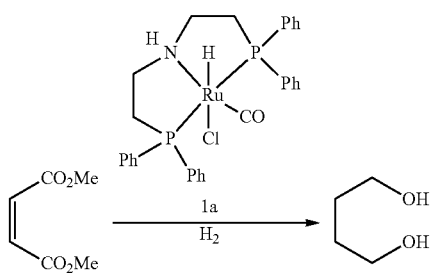

Methyl maleate (4.0 mmol), the complex 1a (0.01 mmol) produced in Example 1, sodium methoxide (0.2 mmol), and methanol (4 mL) were added to a 100 mL autoclave equipped with a stirrer, and the hydrogenation was carried out at 80° C. for 8 hrs with hydrogen pressure of 5 MPa. As a result of the analysis of the reaction for the reaction solution according to gas chromatography, it was found that the reaction conversion rate was 100% and the selectivity was 100%.

Example 23

Hydrogenation of methyl methoxyacetate was carried out according to the following reaction scheme.

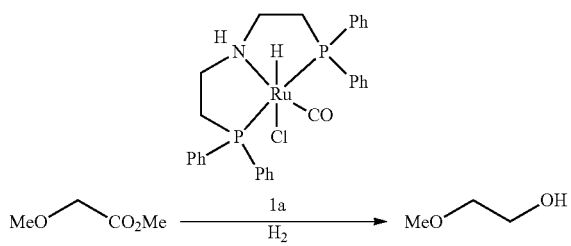

Methyl methoxyacetate (5.0 mmol), the complex 1a (0.01 mmol), sodium methoxide (0.2 mmol), and methanol (4 mL) were added to a 100 mL autoclave equipped with a stirrer, and the hydrogenation was carried out at 80° C. for 8 hrs with hydrogen pressure of 5 MPa. As a result of the analysis of the reaction for the reaction solution according to gas chromatography, it was found that the reaction conversion rate was 100% and the selectivity was 100%.

Comparative Example 1

By using the dichlororuthenium complex described in Patent Document 1, hydrogenation of methyl(R)-lactate was carried out according to the following reaction scheme in the presence of added base.

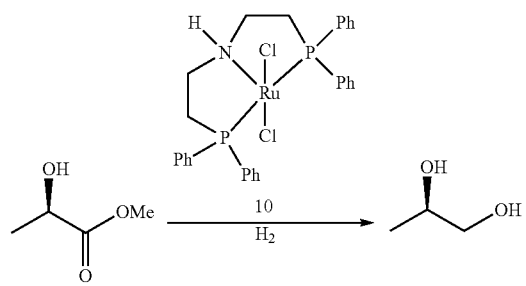

Methyl(R)-lactate (50 mmol), the complex 10 (0.01 mmol), sodium methoxide (0.5 mmol), and tetrahydrofuran (19 mL) were added to a 100 mL autoclave equipped with a stirrer, and the hydrogenation was carried out at 80° C. for 16 hrs with hydrogen pressure of 5 MPa. As a result of the analysis of the reaction solution according to gas chromatography, it was found that the conversion rate was 31%.

Comparative Example 2

Hydrogenation of methyl(R)-lactate was carried out according to the following reaction scheme by using the dichlororuthenium complex that is described in Patent Document 1.

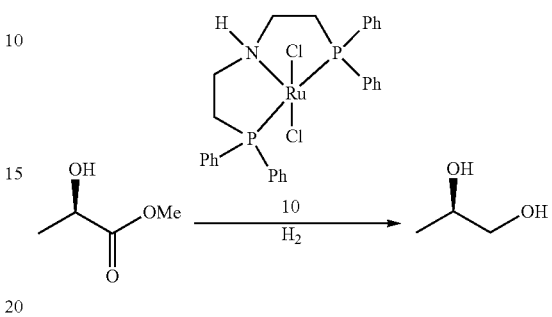

Methyl(R)-lactate (9.95 mmol), the complex 10 (0.01 mmol), sodium methoxide (0.2 mmol), and methanol (4 mL) were added to a 100 mL autoclave equipped with a stirrer, and the hydrogenation was carried out at 30° C. for 16 hrs with hydrogen pressure of 5 MPa. As a result of the analysis of the reaction solution according to gas chromatography, it was found that the conversion rate was 3.5%.

Comparative Example 3

By using the ruthenium carbonyl complex containing an aminodiphosphine ligand in which an ethyl group, instead of a hydrogen atom, is present on the N, hydrogenation of methyl (R)-lactate was carried out according to the following reaction scheme in the presence of added base.

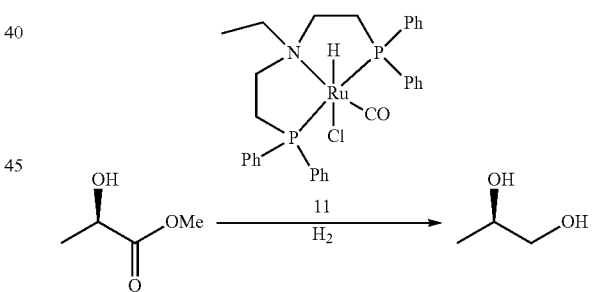

Methyl(R)-lactate (9.95 mmol), the complex 11 (0.01 mmol), sodium methoxide (0.2 mmol), and methanol (4 mL) were added to a 100 mL autoclave equipped with a stirrer, and the hydrogenation was carried out at 30° C. for 16 hrs with hydrogen pressure of 5 MPa. As a result of the analysis of the reaction solution according to gas chromatography, it was found that the conversion rate was 1.2%.

Comparative Example 4

By using the ruthenium carbonyl complex containing an aminodiphosphine ligand in which an ethyl group, instead of a hydrogen atom, is present on the N, hydrogenation of methyl (R)-lactate was carried out according to the following reaction scheme in the presence of added base.

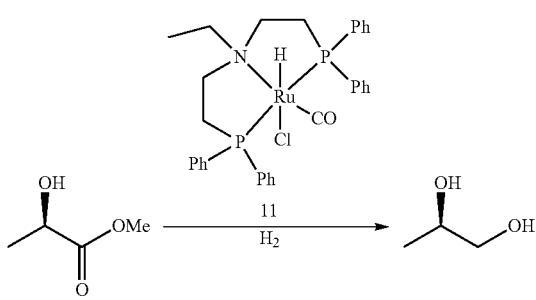

Methyl(R)-lactate (9.95 mmol), the complex 11 (0.002 mmol), sodium methoxide (0.1 mmol), tetrahydrofuran (4 mL) were added to a 100 mL autoclave equipped with a stirrer, and the hydrogenation was carried out at 80° C. for 16 hrs with hydrogen pressure of 5 MPa. As a result of the analysis of the reaction solution according to gas chromatography, it was found that the conversion rate was 1.1%.

Comparative Example 5

By using the ruthenium carbonyl complex 19 (commercially available from Strem Chemicals Inc.) that is described in Non-patent Document 2, hydrogenation of methyl(R)-lactate was carried out according to the following reaction scheme.

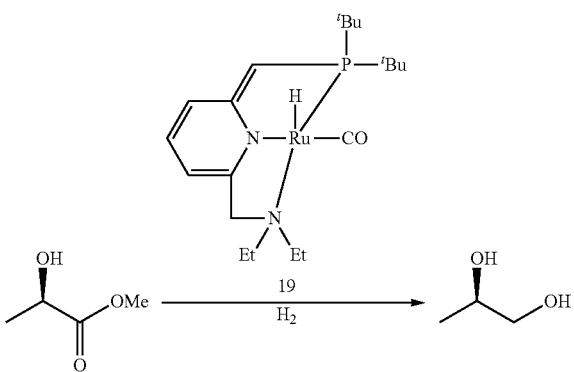

Methyl(R)-lactate (10 mmol), the complex 19 (0.01 mmol), and methanol (8 mL) were added to a 100 mL autoclave equipped with a stirrer, and the hydrogenation was carried out at 30° C. for 16 hrs with hydrogen pressure of 5 MPa. As a result of the analysis of the reaction solution according to gas chromatography, it was found that the conversion rate was 2.6% and the selectivity was 0%.

Comparative Example 6

By using the ruthenium carbonyl complex 19 (commercially available from Strem Chemicals Inc.) that is described in Non-patent Document 2, hydrogenation of methyl(R)-lactate was carried out according to the above reaction scheme in the presence of added base.

Methyl(R)-lactate (10 mmol), the complex 19 (0.01 mmol), sodium methoxide (0.2 mmol), and methanol (8 mL) were added to a 100 mL autoclave equipped with a stirrer, and the hydrogenation was carried out at 30° C. for 16 hrs with hydrogen pressure of 5 MPa. As a result of the analysis of the reaction solution according to gas chromatography, it was found that the conversion rate was 5.8% and the selectivity was 21.5%.

Comparative Example 7

By using the ruthenium carbonyl complex 19 (commercially available from Strem Chemicals Inc.) that is described in Non-patent Document 2, hydrogenation of methyl(R)-lactate was carried out according to the above reaction scheme while using tetrahydrofuran (THF) instead of methanol as a solvent.

Methyl(R)-lactate (10 mmol), the complex 19 (0.01 mmol), and tetrahydrofuran (8 mL) were added to a 100 mL autoclave equipped with a stirrer, and the hydrogenation was carried out at 100° C. for 16 hrs with hydrogen pressure of 5 MPa. As a result of the analysis of the reaction solution according to gas chromatography, it was found that the conversion rate was 7.4% and the selectivity was 40.7%.

Industrial Applicability

The invention is to provide a novel ruthenium carbonyl complex having a tridentate aminodiphosphine ligand that can be conveniently prepared from an easily obtainable inorganic ruthenium compound. The novel ruthenium carbonyl complex of the invention catalyzes the hydrogenation-reduction of ketones, esters, and lactones in the presence of a hydrogen donor, has high catalytic activity even under a relatively mild reaction condition, and also allows the asymmetric hydrogenation-reduction of a carbonyl group. Further, the novel ruthenium carbonyl complex of the invention has high stability and good handleability, and therefore it is suitable for industrial application.

Therefore, the ruthenium carbonyl complex of the invention and the method for hydrogenation-reduction of ketones, esters, and lactones using the same are useful in the field of industrial organic chemistry.

The invention claimed is:

1. A ruthenium carbonyl complex that is represented by Formula (1):

RuXY(CO)(L)                                (1)

wherein X and Y, which may be the same or different from each other, represent an anionic ligand and L represents a tridentate aminodiphosphine ligand represented by Formula (2):

wherein $R^1$, $R^2$, $R^3$, and $R^4$, which may be the same or different from each other, represent a hydrogen atom, an alkyl group, a cycloalkyl group, an aryl group, an aralkyl group, an alkyloxy group, a cycloalkyloxy group, an aryloxy group, an aralkyloxy group, a heterocyclic group, or a substituted amino group, and $R^1$ and $R^2$ or $R^3$ and $R^4$ may bind to each other to form a ring with an adjacent phosphorus atom, the alkyl group, cycloalkyl group, aryl group, aralkyl group, alkyloxy group, cycloalkyloxy group, aryloxy group, aralkyloxy group, heterocyclic group, and substituted amino group may have a substituent group, and $Q^1$ and $Q^2$, which may be the same or different from each other, represent a divalent alkylene group which may have a substituent group, a divalent cycloalkylene group which may have a substituent group, or a divalent aralkylene group which may have a substituent group.

2. The ruthenium carbonyl complex according to claim 1, wherein the tridentate aminodiphosphine ligand L is represented by Formula (3):

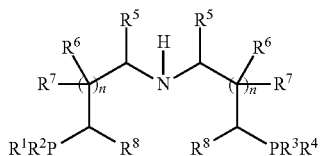
(3)

wherein $R^5$, $R^6$, $R^7$ and $R^8$, which may be the same or different from each other, represent a hydrogen atom, an alkyl group which may have a substituent group, a cycloalkyl group which may have a substituent group, an aryl group which may have a substituent group, or an aralkyl group which may have a substituent group, and n represents an integer of 0 to 3.

3. The ruthenium carbonyl complex according to claim 1, wherein the tridentate aminodiphosphine ligand L is represented by Formula (4):

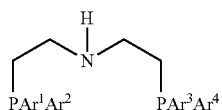
(4)

wherein $Ar^1$, $Ar^2$, $Ar^3$, and $Ar^4$, which may be the same or different from each other, represent an aryl group or an aromatic heterocyclic group, wherein the aryl group and the aromatic heterocyclic group may have a substituent group.

4. The ruthenium carbonyl complex according to claim 3, wherein each of $Ar^1$, $Ar^2$, $Ar^3$, and $Ar^4$ in Formula (4) is a phenyl group which may have a substituent group.

5. The ruthenium carbonyl complex according to claim 1, wherein the tridentate aminodiphosphine ligand L is represented by Formula (5):

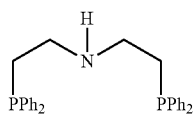
(5)

wherein Ph represents a phenyl group.

6. The ruthenium carbonyl complex according to claim 1, wherein the tridentate aminodiphosphine ligand L is optically active.

7. The ruthenium carbonyl complex according claim 1, wherein the anionic ligand X is a hydride and the anionic ligand Y is a chloride ion in Formula (1).

8. The ruthenium carbonyl complex according to claim 1, wherein the anionic ligand X is a hydride and the anionic ligand Y is $BH_4^-$ in Formula (1).

9. A method of producing a ruthenium carbonyl complex represented by Formula (1):

$$RuXY(CO)(L) \quad (1)$$

wherein X and Y, which may be the same or different from each other, represent an anionic ligand and L represents a tridentate aminodiphosphine ligand represented by Formula (2):

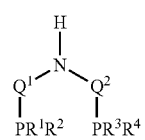
(2)

wherein, $R^1$, $R^2$, $R^3$, and $R^4$, which may be the same or different from each other, represent a hydrogen atom, an alkyl group, a cycloalkyl group, an aryl group, an aralkyl group, an alkyloxy group, a cycloalkyloxy group, an aryloxy group, an aralkyloxy group, a heterocyclic group, or a substituted amino group, and $R^1$ and $R^2$ or $R^3$ and $R^4$ may bind to each other to form a ring with an adjacent phosphorus atom, the alkyl group, cycloalkyl group, aryl group, aralkyl group, alkyloxy group, cycloalkyloxy group, aryloxy group, aralkyloxy group, heterocyclic group, and substituted amino group may have a substituent group, and $Q^1$ and $Q^2$, which may be the same or different from each other, represent a divalent alkylene group which may have a substituent group, a divalent cycloalkylene group which may have a substituent group, or a divalent aralkylene group which may have a substituent group, by reacting the tridentate aminodiphosphine ligand L represented by Formula (2) and $RuXY(CO)(P(Ar^5)_3)_3$, wherein X and Y are as defined above and $Ar^5$ may be the same or different from each other and represents an aryl group which may have a substituent group.

10. The method according to claim 9, wherein $Ar^5$ is a phenyl group.

11. The method according to claim 9, wherein the tridentate aminodiphosphine ligand L represented by Formula (2) is a tridentate aminodiphosphine ligand L represented by Formula (5):

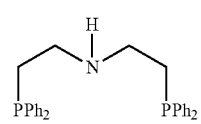
(5)

wherein Ph represents a phenyl group.

12. The method according to claim 9, wherein $RuXY(CO)(P(Ar^5)_3)_3$ is $RuHCl(CO)(PPh_3)_3$.

13. A method of producing a ruthenium carbonyl complex represented by Formula (6):

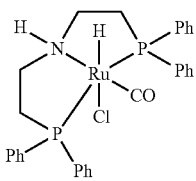
(6)

by reacting RuHCl(CO)(PPh$_3$)$_3$ and a tridentate aminodiphosphine ligand L represented by Formula (5):

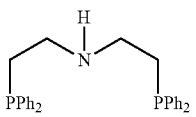
(5)

wherein Ph represents a phenyl group.

14. A method of producing a ruthenium carbonyl complex represented by Formula (7):

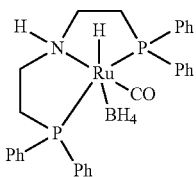
(7)

by reacting a ruthenium carbonyl complex represented by Formula (6):

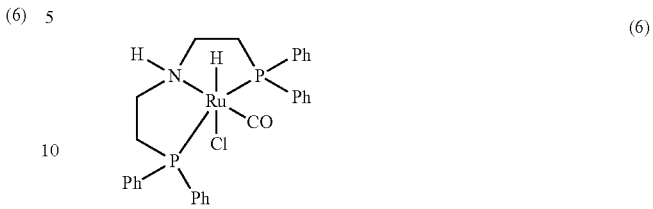
(6)

and NaBH$_4$.

15. A method of producing alcohols, comprising a hydrogenation-reduction of ketones, wherein said hydrogenation-reduction uses a hydrogen donor in the presence of the ruthenium carbonyl complex according to claim 1.

16. A method of producing optically active alcohols, comprising an asymmetric hydrogenation-reduction of ketones, wherein the asymmetric hydrogenation-reduction uses a hydrogen donor in the presence of the ruthenium carbonyl complex according to claim 6.

17. A method of producing alcohols, comprising a hydrogenation-reduction of esters or lactones, wherein said hydrogenation-reduction uses a hydrogen donor in the presence of the ruthenium carbonyl complex according to claim 1.

18. A method of producing optically active alcohols, comprising a hydrogenation-reduction of optically active esters or optically active lactones, wherein said hydrogenation-reduction uses a hydrogen donor in the presence of the ruthenium carbonyl complex according to claim 1, and maintains the optical activity of the esters or the lactones.

* * * * *